United States Patent
Li et al.

(10) Patent No.: US 12,168,654 B2
(45) Date of Patent: *Dec. 17, 2024

(54) PYRIMIDINE DERIVATIVE CONTAINING ONE DEUTERIUM ATOM AND PREPARATION PROCESS AND USE THEREOF

(71) Applicants: Guangdong Lewwin Pharmaceutical Research Institute Co., Ltd., Guangdong (CN); Guangdong CS-Lewwin Drug Research Co., Ltd., Guangdong (CN)

(72) Inventors: Xingshu Li, Guangdong (CN); Xinzi Chen, Guangdong (CN); Wei Yang, Guangdong (CN); Jianmin Guo, Guangdong (CN)

(73) Assignees: Guangdong Lewwin Pharmaceutical Research Institute Co., Ltd., Guangdong (CN); Guangdong CS-Lewwin Drug Research Co., Ltd., Guangdong (CN)

( * ) Notice: Subject to any disclaimer, the term of this patent is extended or adjusted under 35 U.S.C. 154(b) by 830 days.

This patent is subject to a terminal disclaimer.

(21) Appl. No.: 17/156,794

(22) Filed: Jan. 25, 2021

(65) Prior Publication Data

US 2021/0139464 A1 May 13, 2021

Related U.S. Application Data

(63) Continuation of application No. PCT/CN2019/105043, filed on Sep. 10, 2019.

(30) Foreign Application Priority Data

Sep. 12, 2018 (CN) .......................... 201811059596.7
Dec. 28, 2018 (CN) .......................... 201811623543.3

(51) Int. Cl.
| | |
|---|---|
| *C07D 403/10* | (2006.01) |
| *A61K 31/4545* | (2006.01) |
| *A61P 35/00* | (2006.01) |
| *C07B 59/00* | (2006.01) |
| *C07D 239/30* | (2006.01) |
| *C07D 401/12* | (2006.01) |
| *C07D 401/14* | (2006.01) |
| *C07D 403/14* | (2006.01) |

(52) U.S. Cl.
CPC ............ *C07D 403/10* (2013.01); *A61P 35/00* (2018.01); *C07B 59/002* (2013.01); *C07D 239/30* (2013.01); *C07D 401/12* (2013.01); *C07D 401/14* (2013.01); *C07D 403/14* (2013.01); *C07B 2200/05* (2013.01)

(58) Field of Classification Search
CPC .... C07D 403/10; A61K 31/4545; A61P 35/00
See application file for complete search history.

(56) References Cited

U.S. PATENT DOCUMENTS

| | | |
|---|---|---|
| 6,221,335 B1 | 4/2001 | Foster |
| 6,440,710 B1 | 8/2002 | Keinan et al. |
| 6,603,008 B1 | 8/2003 | Ando et al. |
| 7,517,990 B2 | 4/2009 | Ito et al. |
| 8,580,781 B2 | 11/2013 | Dorsch et al. |
| 2007/0082929 A1 | 4/2007 | Gant et al. |
| 2007/0197695 A1 | 8/2007 | Potyen et al. |

FOREIGN PATENT DOCUMENTS

| | | |
|---|---|---|
| CN | 101687857 A | 3/2010 |
| CN | 101743241 A | 6/2010 |
| CN | 102264727 A | 11/2011 |
| CN | 108752322 A | 11/2018 |
| CN | 109608442 A | 4/2019 |

OTHER PUBLICATIONS

Ma et al., Myricetin inhibits migration and invasion of hepatocellular carcinoma MHCC97H cell line by inhibiting the EMT process, Oncology Letters 18, pp. 6614-6620 (2019).*
Simone, Oncology: Introduction, Cecil Textbook of Medicine, 20th Edition, vol. 1, pp. 1004-1010, 1996.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Pearce et al., Failure modes in anticancer drug discovery and development, Cancer Drug Design and Discovery Edited by Stephen Neidle, Chapter 18, pp. 424-435 (2008).*
Acute Leukemia, Merck Manual (Online Edition) 6 pages, pp. 1-6 (2013).*
Baillie, T.A., "The Use of Stable Isotopes in Pharmacological Research", Pharmacological Reviews, vol. 33, No. 2, 1981.
Browne, T.R, "Stable Isotope Techniques in Early Drug Development: An Economic Evaluation", J Clin Pharmacol 1998;38:213-220.
Cherrah, et al., "Study of Deuterium Isotope Effects on Protein Binding by Gas Chromatography/Mass Spectrometry. Caffeine and Deuterated Isotopomers", Biomedical and Environmental Mass Spectrometry, vol. 14, 653-657 (1987).

(Continued)

*Primary Examiner* — Bruck Kifle
(74) *Attorney, Agent, or Firm* — Morse, Barnes-Brown & Pendleton, P.C.; Martin Z. Zhang, Esq.

(57) ABSTRACT

The present invention discloses a pyrimidine derivative containing one deuterium atom, a preparation process thereof and a use thereof. It is demonstrated through in vivo and in vitro animal experiments that the antitumor activity of the pyrimidine derivative containing one deuterium atom provided in the disclosure is significantly superior to that of the positive drug Tepotinib, and the preparation process is simple and low in cost.

13 Claims, 4 Drawing Sheets

(56) References Cited

OTHER PUBLICATIONS

Dorsch, D., "Identification and optimization of pyridazinones as potent and selective c-Met kinase inhibitors", Bioorganic & Medicinal Chemistry Letters, 25 (2015) 1597-1602.

Dyck, L.E., "Effects of Deuterium Substitution on the Catabolism of β-Phenylethylamine: An In Vivo Study", Journal of Neurochemistry, vol. 46, No. 2, 1986.

Gouyette, A., "Synthesis of Deuterium-labelled Elliptinium and its Use in Metabolic Studies", Biomedical and Environmental Mass Spectrometry, vol. 15, 243-247 (1988).

Haskins, N.J., "The Application of Stable Isotopes in Biomedical Research", Biomedical Mass Spectrometry, vol. 9, No. 7, 1982.

Honma et al., "The Metabolism of Roxatidine Acetate Hydrochloride Liberation of Deuterium from the Piperidine Ring during Hydroxylation", Drug Metabolism and Disposition, vol. 15, No. 4, Mar. 17, 1987.

Jia et al., "Discovery of (S)-1-(1-(Imidazo[1,2-a]pyridin-6-yl)ethyl)-6-(1-methyl-1 H-pyrazol-4-yl)-1 H-[1,2,3]triazolo[4,5-b] pyrazine (Volitinib) as a Highly Potent and Selective Mesenchymal-Epithelial Transition Factor (c-Met) Inhibitor in Clinical Development for Treatment of Cancer", Journal of Medicinal Chemistry, 2014, 57, 7577-7589.

Pieniaszek, Jr. et al., Moricizine Bioavailability via Simultaneous, Dual, Stable Isotope Administration: Bioequivalence Implications, J Clin Pharmacol 1999;39:817-825.

Pubchem CID 25171648, Create Date: Mar. 3, 2009; Date Accessed: Oct. 27, 2022; Tepotinib, 35 pages.

Tonn et al., "Simultaneous Analysis of Diphenhydramine and a Stable Isotope Analog (2H10)Diphenhydramine Using Capillary Gas Chromatography with Mass Selective Detection in Biological Fluids from Chronically Instrumented Pregnant Ewes", Biological Mass Spectrometry, vol. 22, 633-642 (1993).

Non-Final Office Action in U.S. Appl. No. 18/223,652 dated Aug. 1, 2024.

* cited by examiner

PYRIMIDINE DERIVATIVE CONTAINING ONE DEUTERIUM ATOM AND PREPARATION PROCESS AND USE THEREOF

CROSS REFERENCE TO RELATED APPLICATIONS

This application is a continuation of International Application No. PCT/CN2019/105043, filed on Sep. 10, 2019, which claims priority to Chinese Application No. 201811059596.7, filed on Sep. 12, 2018, and Chinese Application No. 201811623543.3, filed on Dec. 28, 2018, the contents of all prior applications being hereby incorporated by reference in their entirety.

TECHNICAL FIELD

The present invention relates to the field of medicaments, in particular relates to a pyrimidine derivative containing one deuterium atom, a preparation process thereof and a use thereof in the anti-tumor drugs.

BACKGROUND

Cancer is one of the major diseases that seriously endanger people's health. According to the 2017 national cancer statistics released by the National Cancer Center, there were 3.804 million novel cases of malignant tumors in China, corresponding to that more than 10,000 people were diagnosed with cancer on average every day. The top five cancers in urban areas are lung cancer, colorectal cancer, gastric cancer, liver cancer, and female breast cancer; and the top five cancers in rural areas are lung cancer, gastric cancer, liver cancer, esophagus cancer, and colorectal cancer. Therefore, it is very important to find and develop novel effective anticancer drugs.

c-Met proto-oncogenes belong to Ron subfamily of protein tyrosine kinases (PTKs) family, the c-Met proteins which encode are the only high-affinity receptors of hepatocyte growth factor/scatter factor (HGF/SF). HGF/c-Met signaling pathway is closely related to angiogenesis and tumor growth, so inhibition of the pathway has become a novel strategy for the targeted anti-tumor therapy. There have been many studies in the literatures about the design, synthesis and anti-tumor activities of novel c-Met inhibitors, wherein Tepotinib (EMD1214063) is a highly selective and potent small molecule c-Met inhibitor developed by Merck Serono. Currently, phase 2 clinical trials of hepatocellular carcinoma have been conducted on Tepotinib with positive results, and it is very likely to be approved as a novel important anti-cancer drug. However, Tepotinib has its own defects due to the presence of sites that are prone to metabolism in its molecule, showing the disadvantage of low bioavailability in the PK data of dogs and monkeys. Chirality is a basic feature of nature, and several important substances that constitute the phenomenon of life, such as saccharides, proteins, nucleic acids, enzymes and cell surface receptors, all possess chirality. Both human beings and other biological systems have complex chiral environments, and organisms can be accurately recognized by chiral molecules. This kind of specific recognition and chirality has extremely important significance to human health and living environment. When chiral drugs act on organisms, drug molecules with the same composition but different configurations often have different pharmacological and toxic side effects. Therefore, chirality plays a unique role in the process of life, and chiral drugs have attracted more and more attention.

Deuterium (D or $^2H$) is a stable non-radioactive isotope of hydrogen. The zero-point vibration energy of carbon-deuterium bond is lower than that of carbon-hydrogen bond, so it's more stable. The replacement of metabolizable sites in drug molecules by deuterium may directly affect the absorption, distribution, metabolism of drugs, producing the effects of improving the efficacy of drugs, closing the metabolism sites and prolonging the half-life of drugs. Deuterated drugs, as a new class of drugs, has caused extensive concern at domestic and abroad.

SUMMARY

To overcome the defects in the prior art, the present invention aims to provide a novel pyrimidine derivative with good bioavailability and anti-tumor activity.

Another object of the invention is to provide a process for preparing the novel pyrimidine derivative.

A further object of the invention is to provide a use of the novel pyrimidine derivative in the preparation of anti-tumor drugs.

The objects of the invention are achieved through the following technical schemes:

A novel pyrimidine derivative, the structural formula of which is as shown below:

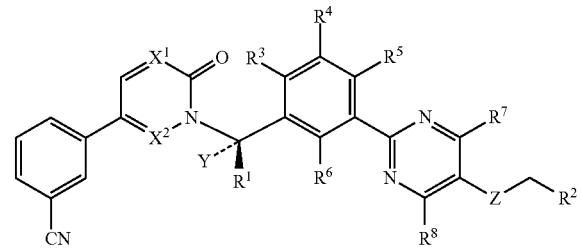

General structural formula of the novel pyrimidine derivatives wherein, $X^1$ and $X^2$ indicate, independently of one another, CH or N; Y is a hydrogen atom or an isotope of hydrogen (deuterium); $R^1$ is a hydrogen atom, an isotope of hydrogen (deuterium), an alkyl, alkenyl or alkynyl containing one to four carbons, wherein one or more hydrogen atoms in the alkyl, alkenyl or alkynyl can be substituted with the isotope of hydrogen (deuterium); Z is an oxygen atom, a sulfur atom, a selenium atom, NH, $NCH_3$ or sulfoxide SO; $R^2$ is 2-(N,N-dialkylamino)ethyl, or 4-piperidyl with the nitrogen atom attached to an alkyl containing 1 to 4 carbons, or 4-piperidyl with positions 2, 3 substituted with an alkyl, or 4-piperidyl with a bridge ring; $R^3$-$R^8$ are each, independently of one another, a hydrogen atom, a halogen or an alkyl, alkenyl or alkynyl containing one to four carbons.

Preferably, $X^1$ and $X^2$ indicate, independently of one another, CH or N; Y is a hydrogen atom or an isotope of hydrogen (deuterium); $R^1$ is a hydrogen atom, an isotope of hydrogen (deuterium), $CH_3$ group, $CD_3$ group, or an alkyl, alkenyl or alkynyl containing two to four carbons, or a deuterium-substituted hydrocarbyl; Z is an oxygen atom, a sulfur atom, a selenium atom, NH, $NCH_3$ or sulfoxide SO; $R^2$ is 2-(N,N-dialkylamino)ethyl, or 4-piperidyl with the nitrogen atom attached to an alkyl containing 1 to 4 carbons, e.g., N-methyl 4-piperidyl, N-ethyl 4-piperidyl; $R^3$-$R^8$ are hydrogen atoms.

Preferably, $X^1$ and $X^2$ may be, separately or simultaneously, carbon atoms or nitrogen atoms; when $X^1$ is an carbon atom, $X^2$ is a nitrogen atom, B ring is of a pyridazinone structure; when $X^1$ is a nitrogen atom, $X^2$ is an carbon atom, B ring is of a cyclic urea structure; when $X^1$ and $X^2$ are both carbon atoms, B ring is of an amide structure.

Preferably, the novel pyrimidine derivative is a chiral derivative, there being a chiral carbon atom in the molecule. That is, Y is a hydrogen atom or an isotope of hydrogen (deuterium), $R^1$ is $CH_3$, $C_2H_5$, $CD_3$, $C_2D_5$ or an alkyl, alkenyl or alkynyl containing two to four carbons, wherein one or more hydrogen atoms in the alkyl, alkenyl or alkynyl can be substituted with the isotope of hydrogen (deuterium); the carbon attached with $R^1$ and Y is a chiral carbon, thus resulting in optical chiral isomers in two different configurations, R-configuration and S-configuration.

Preferably, in the novel pyrimidine derivative, hydrogen is substituted with deuterium at the sites that are prone to metabolism. That is, at least one of Y and $R^1$ contains an isotope of hydrogen (deuterium), so that it has better pharmacokinetic effects. For example, Y may be an isotope of hydrogen (deuterium), and $R^1$ may be an isotope of hydrogen (deuterium) or a deuterated methyl $CD_3$, a deuterated ethyl $C_2D_5$.

Preferably, the side chain of the novel pyrimidine derivative contains a structure of thioether, sulfoxide SO or selenide. That is, Z is a sulfur atom, a selenium atom or a sulfoxide SO group, so that it can produce other pharmaceutical properties.

More preferably, the novel pyrimidine derivative is a chiral deuterated derivative. That is, Y is an isotope of hydrogen (deuterium), $R^1$ is $CH_3$ or an alkyl, alkenyl or alkynyl containing two to four carbons, the carbon attached with $R^1$ and Y is a chiral carbon, thus resulting in optical chiral deuterated isomers in two different configurations, R-configuration and S-configuration.

More preferably, the novel pyrimidine derivative is a chiral deuterated derivative. That is, Y is a hydrogen atom, $R^1$ is $CD_3$, $C_2D_5$ or other deuterated hydrocarbyl, the carbon attached with $R^1$ and Y is a chiral carbon, thus resulting in optical chiral deuterated isomers in two different configurations, R-configuration and S-configuration.

More preferably, the novel pyrimidine derivative is a chiral deuterated derivative. That is, Y is an isotope of hydrogen (deuterium), $R^1$ is $CD_3$, $C_2D_5$ or deuterated hydrocarbyl, the carbon attached with $R^1$ and Y is a chiral carbon, thus resulting in optical chiral deuterated isomers in two different configurations, R-configuration and S-configuration.

Most preferably, the novel pyrimidine derivative is a chiral deuterated derivative, which has a chiral structure, hydrogen is substituted with deuterium at the sites that are prone to metabolism, and the side chain contains a structure of thioether, sulfoxide SO or selenide; that is, the carbon attached with $R^1$ and Y is a chiral carbon; at least one of Y and $R^1$ contains an isotope of hydrogen (deuterium); Z is a sulfur atom, a selenium atom or a sulfoxide SO group.

All the above mentioned optical chiral isomers or optical chiral deuterated isomers in R-configuration and S-configuration all have good anti-tumor cell proliferation activities; more preferably, optical chiral isomers or optical chiral deuterated isomers in R-configuration show better results in experiments of anti-tumor cell proliferation activities.

When the novel pyrimidine derivative has no chiral centers, or has a chiral center but is a racemate (racemate means that the two configurations (R and S) are in equal amounts), its preparation process includes the following steps:

(1) Reacting 2-chloro-5-fluoropyrimidine with a phenylboronic acid derivative with hydroxymethyl at position 3 to obtain an intermediate 3; or reacting 2-chloro-5-fluoropyrimidine with a phenylboronic acid derivative with acetyl at position 3 to obtain an intermediate 2, then reducing with sodium borohydride to obtain an intermediate 3;

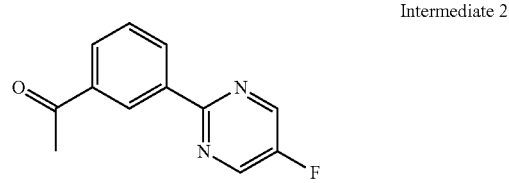

Intermediate 2

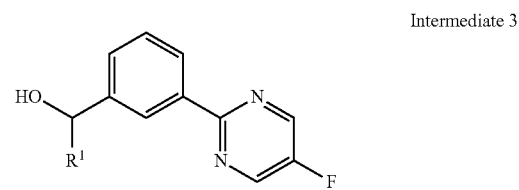

Intermediate 3

(2) Reacting the intermediate 3 with dichlorosulfoxide in chloroform, after the alcoholic hydroxyl being substituted with chlorine, a nucleophilic substitution occurred with pyridinyl-carrying pyridazinone or cyclic urea derivatives to obtain an intermediate 4 (wherein $R^3$, $R^4$ are —F, or $R^3$ is —CN, $R^4$ is —H);

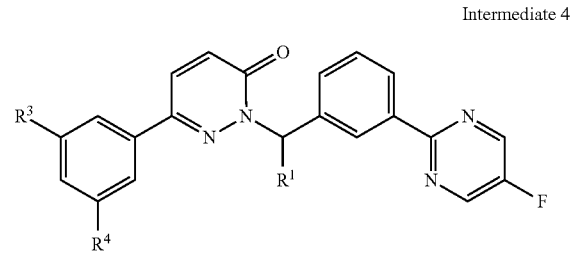

Intermediate 4

(3) Reacting the intermediate 4 with a linear or cyclic amino alcohol in sodium hydride/N,N-dimethyl formamide to obtain an achiral or racemic pyrimidine derivative 5; or, reacting the intermediate 4 with thiol to obtain an achiral or racemic pyrimidine derivative 6; or, reacting the intermediate 4 with selenol to obtain an achiral or racemic pyrimidine derivative 7, the general structural formulas of the achiral or racemic pyrimidine derivatives 5, 6, 7 are as shown below, wherein X is an oxygen atom, a sulfur atom or a selenium atom.

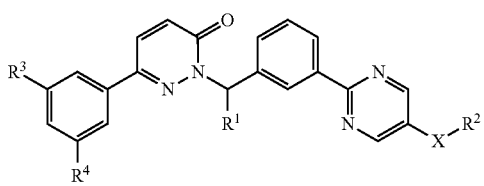

General structural formulas of pyrimidine derivatives 5, 6, 7

In step 3, the thiol or selenol is obtained from the hydrolysis of fatty amino isothiourea or fatty amino isoselenourea over a one-pot process.

When the novel pyrimidine derivative has no chiral centers, or has a chiral center but is a racemate, its specific synthesis route is as shown in FIG. 1.

Wherein, the reagents and reaction conditions for each step are:

Step a: the molar ratio of 2-chloro-5-fluoropyrimidine, a phenylboronic acid derivative with hydroxymethyl or acetyl at position 3, bis(triphenyl phosphine) palladium dichloride and sodium carbonate is (33 to 51.5):(32 to 50):(0.33 to 0.52):(66 to 103), the solvent is toluene/water/ethanol at a mass ratio of 1:1:2, the reaction temperature is 80 to 100° C., and the reaction time is 8 to 10 hours;

Step b: the molar ratio of the intermediate 2 and sodium borohydride is (10 to 30):(15 to 45), the solvent is isopropanol, reacting at 0 to 4° C. for 1 to 2 hours, then at 25 to 35° C. for 1 to 2 hours to obtain the intermediate 3;

Step c: firstly, reacting the intermediate 3 with dichlorosulfoxide, the reaction temperature is 30 to 40° C., and the reaction time is 2 to 4 hours; then adding potassium carbonate, the solvent is N-methyl pyrrolidinone, continue to reaction, the reaction temperature is 80 to 100° C., and the reaction time is 20 to 24 hours to obtain the intermediate 4; wherein, the molar ratio of the intermediate 3, dichlorosulfoxide and potassium carbonate is (5 to 15):(25 to 75):(10 to 30);

Step d: preparation of the achiral or racemic pyrimidine derivative 5: the molar ratio of the intermediate 4, sodium hydride (at a mass concentration of 60%), and 3-(dimethylamino)-1-propanol/1-methyl piperidine-4-methanol is (1 to 4):(1.5 to 6):(1.2 to 4.8), the solvent is N,N-dimethyl formamide, reacting at 0 to 4° C. for 15 to 30 minutes, then at 25 to 30° C. for 1 to 2 hours to obtain the achiral or racemic pyrimidine derivative 5;

Preparation of the achiral or racemic pyrimidine derivative 6 and the achiral or racemic pyrimidine derivative 7: (i) firstly, the molar ratio of thiourea or selenourea and R₂CH₂Cl is (2 to 10):(2 to 10), the solvent is absolute ethyl alcohol, obtaining alkylamino isothiourea or alkylamino isoselenourea; (ii) then, the molar ratio of the intermediate 4, alkylamino isothiourea or alkylamino isoselenourea, and sodium hydroxide is (1 to 5):(2 to 10):(4 to 20), the solvent is N,N-dimethyl formamide/water (with a mass ratio of 5:1), reacting at 25 to 35° C. for 15 to 30 minutes, then at 60 to 80° C. for 3 to 6 hours to obtain the achiral or racemic pyrimidine derivative 6 or 7.

When the novel pyrimidine derivative is a chiral oxygen-containing derivative, its preparation process includes the following steps:

(1) Reacting 2-chloro-5-fluoropyrimidine with a phenylboronic acid derivative with acetyl at position 3 to obtain the intermediate 2; reacting the intermediate 2 with linear or cyclic amino alcohol in the presence of sodium hydride to obtain an intermediate 8;

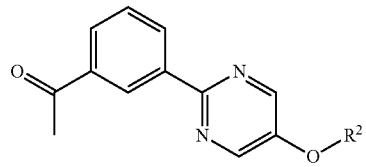

Intermediate 8

(2) Conducting an asymmetric hydrogen transfer reaction of the intermediate 8 in the presence of a catalyst dichloro(p-cymene) ruthenium (II) dimer and a chiral ligand (S,S)-CsDPEN or (R,R)-CsDPEN to obtain a chiral alcohol intermediate 9;

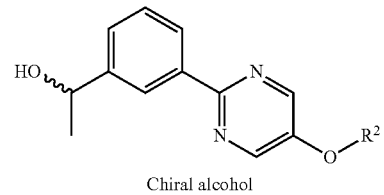

intermediate 9

Chiral alcohol (3) Conducting Mitsunobu reaction between the alcohol intermediate 9 in S-configuration and cyano-carrying pyridazinone to obtain a chiral pyrimidine derivative 5 with an inverted configuration, R-configuration; conducting Mitsunobu reaction between the alcohol intermediate 9 in R-configuration and cyano-carrying pyridazinone to obtain a chiral pyrimidine derivative 5 with an inverted configuration, S-configuration; wherein, the structural formula of the chiral pyrimidine derivative 5 in R-configuration or S-configuration is as shown below.

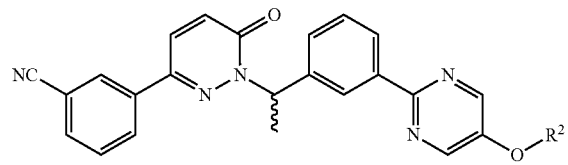

Chiral pyrimidine derivative 5 in R-configuration or S-configuration

When the novel pyrimidine derivative is a chiral oxygen-containing derivative, its specific synthesis route is as shown in FIG. 2.

Wherein, the reagents and reaction conditions for each step are:

Step a: the molar ratio of the intermediate 2, sodium hydride (at a mass concentration of 60%), and 3-(dimethylamino)-1-propanol or 1-methyl piperidine-4-methanol is (5.0 to 20):(7.5 to 30):(6.0 to 24), the solvent is N,N-dimethyl formamide, reacting at 0 to 4° C. for 15 to 30 minutes, then at 25 to 35° C. for 1 to 4 hours to obtain the intermediate 8;

Step b: firstly adding cymene ruthenium (II) dichlorodimer, (S,S)-CsDPEN or (R,R)-CsDPEN, the solvent is water, reacting at 25 to 40° C. under the protection of nitrogen for 4 to 8 hours; then adding the intermediate 8 and sodium formate, the solvent is dichloromethane/ H₂O (with a mass ratio of 2:1), reacting at 25 to 40° C. for 8 to 20 hours to obtain the chiral alcohol intermediate 9; wherein, the molar ratio of cymene ruthenium (II) dichlorodimer, (S,S)-CsDPEN or (R,R)-CsDPEN, the intermediate 8, and sodium formate is (0.01 to 0.04):(0.02 to 0.08):(1.0 to 4.0):(5.0 to 20.0);

Step c: the molar ratio of the chiral alcohol intermediate 9, 3-(6-oxo-1,6-dihydropyridazin-3-yl)-benzonitrile, triphenyl phosphine, and diisopropyl azodicarboxylate is (0.5 to 2.5):(0.5 to 2.5):(0.75 to 3.75):(0.75 to 3.75), the solvent is tetrahydrofuran/N,N-dimethyl formamide (with a mass ratio of 10:1), firstly reacting at 0 to 4° C. for 1 to 30 minutes, then at 25 to 35° C. for 18 to 24 hours to obtain the chiral pyrimidine derivative 5 in R-configuration or S-configuration.

When the novel pyrimidine derivative is a chiral sulfur-containing or selenium-containing derivative, its preparation process includes the following steps:

(1) Reacting 2-chloro-5-fluoropyrimidine with a phenylboronic acid derivative with acetyl at position 3 to obtain the intermediate 2; conducting an asymmetric hydrogen transfer reaction of the intermediate 2 in the presence of the catalyst cymene ruthenium (II) dichlorodimer and the chiral ligand (S,S)-CsDPEN or (R,R)-CsDPEN to obtain a chiral alcohol intermediate 3;

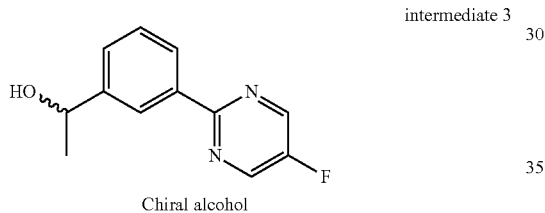

intermediate 3

Chiral alcohol (2) Reacting the chiral alcohol intermediate 3 with thiol to obtain a chiral sulfur-containing intermediate 10; or, reacting the chiral alcohol intermediate 3 with selenol to obtain a chiral selenium-containing intermediate 11; wherein, the structural formula of the chiral sulfur-containing intermediate 10 or the chiral selenium-containing intermediate 11 is as shown below;

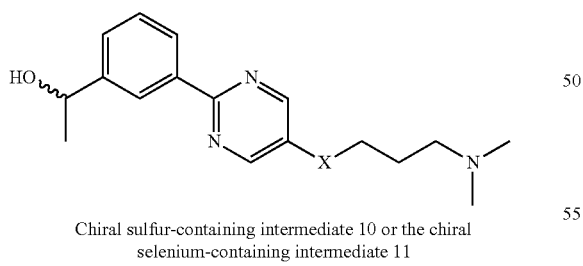

Chiral sulfur-containing intermediate 10 or the chiral selenium-containing intermediate 11

(3) Conducting Mitsunobu reaction between the chiral sulfur-containing intermediate 10 or the chiral selenium-containing intermediate 11 in S-configuration and cyano-carrying pyridazinone to obtain chiral pyrimidine derivatives 6f and 7j in an inverted configuration, R-configuration; conducting Mitsunobu reaction between the chiral sulfur-containing intermediate 10 or the chiral selenium-containing intermediate 11 in R-configuration and cyano-carrying pyridazinone to obtain chiral pyrimidine derivatives 6f and 7j in an inverted configuration, S-configuration; wherein, the structural formula of the chiral pyrimidine derivatives 6f and 7j in R-configuration or S-configuration is as shown below.

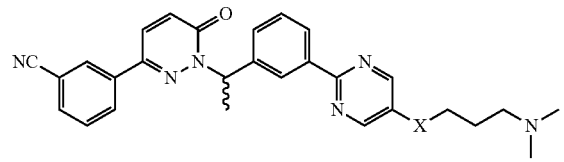

Structural formula of chiral pyrimidine derivative
6f and 7j in R-configuration or S-configuration When the novel pyrimidine derivative is a chiral sulfur-containing or selenium-containing derivative, its specific synthesis route is as shown in FIG. 3.

Wherein, the reagents and reaction conditions for each step are:

Step a: firstly adding cymene ruthenium (II) dichlorodimer, (S,S)-CsDPEN or (R,R)-CsDPEN, the solvent is water, under the protection of nitrogen, reacting at 25 to 40° C. for 4 to 8 hours; then adding the intermediate 2 and sodium formate, the solvent is dichloromethane/water (with a mass ratio of 2:1), reacting at 25 to 35° C. for 8 to 12 hours to obtain a chiral alcohol intermediate 3; wherein, the molar ratio of cymene ruthenium (II) dichlorodimer, (S,S)-CsDPEN or (R,R)-CsDPEN, the intermediate 2, and sodium formate is (0.05 to 0.25):(0.10 to 0.50):(5.0 to 25):(25.0 to 125);

Step b: (i) firstly, the molar ratio of thiourea or selenourea to N,N-dimethylamino chloropropane hydrochloride is (2 to 10):(2 to 10), the solvent is absolute ethyl alcohol, obtaining N,N-dimethylamino propyl isothiourea or N,N-dimethylamino propyl isoselenourea; (ii) then, the molar ratio of the chiral alcohol intermediate 3, N,N-dimethylamino propyl isothiourea or N,N-dimethylamino propyl isoselenourea, and sodium hydroxide is (1 to 5):(2 to 10):(4 to 20), the solvent is N,N-dimethyl formamide/water (with a mass ratio of 5:1), firstly reacting at 25 to 35° C. for 15 to 30 minutes, then at 60 to 80° C. for 3 to 8 hours to obtain a chiral sulfur-containing intermediate 10 or a chiral selenium-containing intermediate 11;

Step c: the molar ratio of the chiral sulfur-containing intermediate 10 or the chiral selenium-containing intermediate 11, 3-(6-oxo-1,6-dihydropyridazin-3-yl)-benzonitrile, triphenyl phosphine, and diisopropyl azodicarboxylate is (0.5 to 2.5):(0.5 to 2.5):(0.75 to 3.75): (0.75 to 3.75), the solvent is tetrahydrofuran/N,N-dimethyl formamide (with a mass ratio of10:1), firstly reacting at 0 to 4° C. for 15 to 30 minutes, then at 25 to 35° C. for 18 to 24 hours to obtain chiral pyrimidine derivatives 6f and 7j in R-configuration or S-configuration.

When the novel pyrimidine derivative is a chiral oxygen-containing deuterated derivative, its preparation process includes the following steps:

(1) In deuterated chloroform, substituting hydrogens on the methyl next to the carbonyl in the intermediate 8b with deuterium to obtain a deuterated intermediate 12;

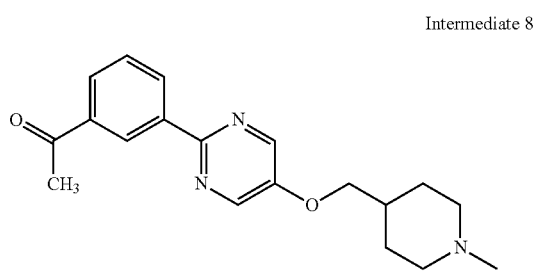

Intermediate 8b

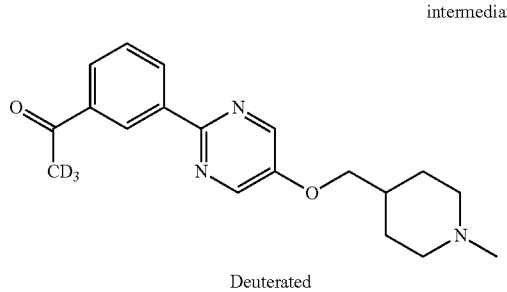

intermediate 12

Deuterated (2) Conducting a chiral hydrogen transfer reaction between the deuterated intermediate 12 and sodium formate or deuterated sodium formate in the presence of the catalyst cymene ruthenium (II) dichlorodimer and the ligand (S,S)-CsDPEN or (R,R)-CsDPEN to obtain a deuterated intermediate 13;

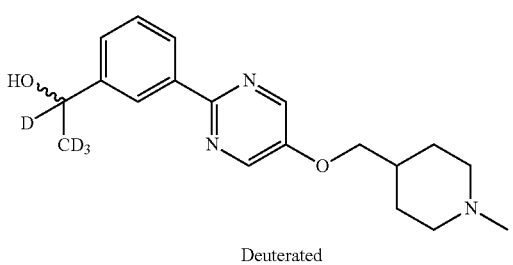

intermediate 13

Deuterated (3) Conducting Mitsunobu reaction between the deuterated intermediate 13 in S-configuration and cyano-carrying pyridazinone to obtain a chiral oxygen-containing deuterated pyrimidine derivative 14 in an inverted configuration, R-configuration; conducting Mitsunobu reaction between the deuterated intermediate 13 in R-configuration and cyano-carrying pyridazinone to obtain a chiral oxygen-containing deuterated pyrimidine derivative 14 in an inverted configuration, S-configuration; Wherein, the structural formula of the chiral oxygen-containing deuterated pyrimidine derivative 14 in R-configuration or S-configuration is as shown below.

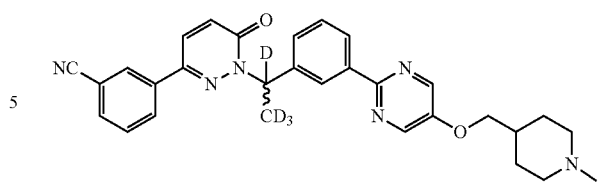

Chiral oxygen-containing deuterated pyrimidine derivative 14 in R-configuration or S-configuration When the novel pyrimidine derivative is a chiral oxygen-containing deuterated derivative, its specific synthesis route is as shown in FIG. 4.

Wherein, the reagents and reaction conditions for each step are:

Step a: the molar ratio of the intermediate 8b to 1,5,7-triazabicyclo[4.4.0]dec-5-ene (TBD) is (5 to 25):(0.5 to 2.5), the solvent is deuterated chloroform, reacting at 25 to 40° C. for 18 to 24 hours to obtain a deuterated intermediate 12;

Step b: racemate: the molar ratio of the deuterated intermediate 12 to sodium borodeuteride is (1.0 to 5.0):(2.0 to 10), the solvent is deuterated methanol, reacting at 0 to 4° C. for 1 to 2 hours, and reacting at 25 to 35° C. for 1 to 4 hours to obtain an intermediate (±)-13;

Optical isomer: the molar ratio of the deuterated intermediate 12, deuterated sodium formate, cymene ruthenium (II) dichlorodimer, and (S,S)-CsDPEN or (R,R)-CsDPEN is (1.0 to 5.0):(5.0 to 25):(0.05 to 0.25):(0.10 to 0.5), the solvent is dichloromethane/water (with a mass ratio of 2:1), reacting at 25 to 35° C. for 8 to 10 hours to obtain an intermediate (R)-13 or (S)-13;

Step c: the molar ratio of the intermediate (±)-13 or (R)-13 or (S)-13, 3-(6-oxo-1,6-dihydropyridazin-3-yl)-benzonitrile, triphenyl phosphine, and diisopropyl azodicarboxylate is (0.5 to 2.5):(0.5 to 2.5):(0.75 to 3.75):(0.75 to 3.75), the solvent is tetrahydrofuran/N,N-dimethyl formamide (with a mass ratio of 10:1), firstly reacting at 0 to 4° C. for 15 to 30 minutes, then at 25 to 40° C. for 18 to 24 hours to obtain a chiral oxygen-containing deuterated pyrimidine derivative 14 in R-configuration or S-configuration.

When the novel pyrimidine derivative is a chiral sulfur-containing deuterated derivative, its preparation process includes the following steps:

(1) In deuterated chloroform, substituting hydrogens on the methyl next to the carbonyl in the intermediate 2 with deuterium to obtain a deuterated intermediate 15;

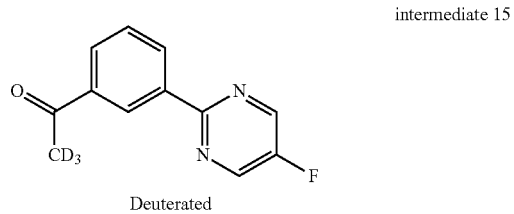 [SMILES: [2H]C([2H])([2H])C(=O)c1cccc(-c2ncc(F)cn2)c1]

intermediate 15

Deuterated (2) Conducting an asymmetric hydrogen transfer reaction on the deuterated intermediate 15 in the presence of the catalyst cymene ruthenium (II) dichlorodimer and the chiral ligand (S,S)-CsDPEN or (R,R)-CsDPEN, to obtain a chiral alcohol intermediate 16;

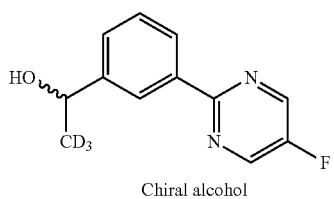

Chiral alcohol (3) Reacting thiol with the chiral alcohol intermediate 16 to obtain a sulfur-containing deuterated intermediate 17;

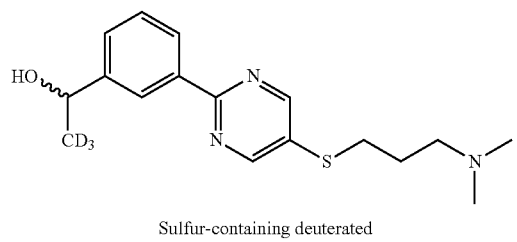

Sulfur-containing deuterated (4) Conducting Mitsunobu reaction between the sulfur-containing deuterated intermediate 17 in S-configuration and cyano-carrying pyridazinone to obtain a chiral pyrimidine derivative 18 in an inverted configuration, R-configuration; conducting Mitsunobu reaction between the sulfur-containing deuterated intermediate 17 in R-configuration and cyano-carrying pyridazinone to obtain a chiral deuterated pyrimidine derivative 18 in an inverted configuration, S-configuration; wherein, the structural formula of the chiral deuterated pyrimidine derivative 18 in R-configuration or S-configuration is as shown below.

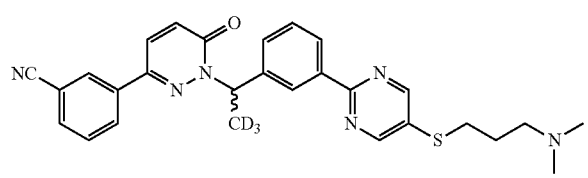

Structural formula of the chiral deuterated pyrimidine derivative 18 in R-configuration or S-configuration When the novel pyrimidine derivative is a chiral sulfur-containing deuterated derivative, its specific synthesis route is as shown in FIG. 5.

Wherein, the reagents and reaction conditions for each step are:

Step a: the molar ratio of the intermediate 2 to 1,5,7-triazabicyclo[4.4.0]dec-5-ene (TBD) is (5 to 25):(0.5 to 2.5), the solvent is deuterated chloroform, reacting at 25 to 35° C. for 18 to 24 hours to obtain a deuterated intermediate 15;

Step b: racemate: the molar ratio of the deuterated intermediate 15 to sodium borodeuteride is (1.0 to 5.0):(2.0 to 10), the solvent is deuterated methanol, firstly reacting at 0 to 4° C. for 1 to 2 hours, then at 25 to 35° C. for 1 to 3 hours to obtain an intermediate (±)-16;

Optical isomer: the molar ratio of the deuterated intermediate 15, deuterated sodium formate, cymene ruthenium (II) dichlorodimer, and (S,S)-CsDPEN or (R,R)-CsDPEN is (1.0 to 5.0):(5.0 to 25):(0.05 to 0.25):(0.10 to 0.25), the solvent is dichloromethane/water (with a mass ratio of 2:1), reacting at 25 to 35° C. for 8 to 12 hours to obtain a chiral alcohol intermediate 16;

Step c: (i) the molar ratio of thiourea to N,N-dimethylamino chloropropane hydrochloride is (2 to 10):(2 to 10), the solvent is absolute ethyl alcohol, obtaining N,N-dimethylamino propyl isothiourea; (ii) the molar ratio of the chiral alcohol intermediate 16, N,N-dimethylamino propyl isothiourea, and sodium hydroxide is (1 to 5):(2 to 10):(4 to 20), the solvent is N,N-dimethyl formamide/water (with a mass ratio of 5:1), firstly reacting at 25 to 35° C. for 15 to 30 minutes, then reacting at 60 to 70° C. for 3 to 6 hours to obtain a sulfur-containing deuterated intermediate 17.

Step d: the molar ratio of the sulfur-containing deuterated intermediate 17, 3-(6-oxo-1,6-dihydropyridazin-3-yl)-benzonitrile, triphenyl phosphine, and diisopropyl azodicarboxylate is (0.5 to 2.5):(0.5 to 2.5):(0.75 to 3.75):(0.75 to 3.75), the solvent is tetrahydrofuran/N,N-dimethyl formamide (with a mass ratio of 10:1), firstly reacting at 0 to 4° C. for 15 to 30 minutes, then at 25 to 35° C. for 18 to 24 hours to obtain a chiral deuterated pyrimidine derivative 18 in R-configuration or S-configuration.

In the present disclosure, when in Formula 2, X1 indicates CH, X2 indicates N, Y is an isotope of hydrogen, deuterium, R1 is an alkyl containing one carbon, Z is an oxygen atom, R2 is 4-piperidyl with the nitrogen atom attached to an alkyl containing 1 carbon, and R3-R8 are hydrogen atoms, the pyrimidine derivative is a pyrimidine derivative containing one deuterium atom, labelled as (R)-1D288:

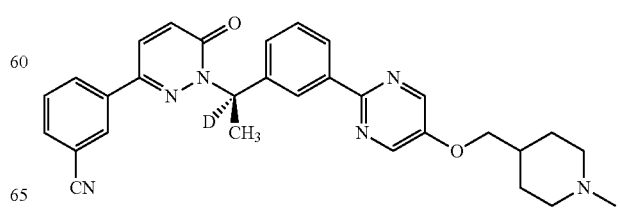

The synthetic route of (R)-1D288 is shown in Formula A:

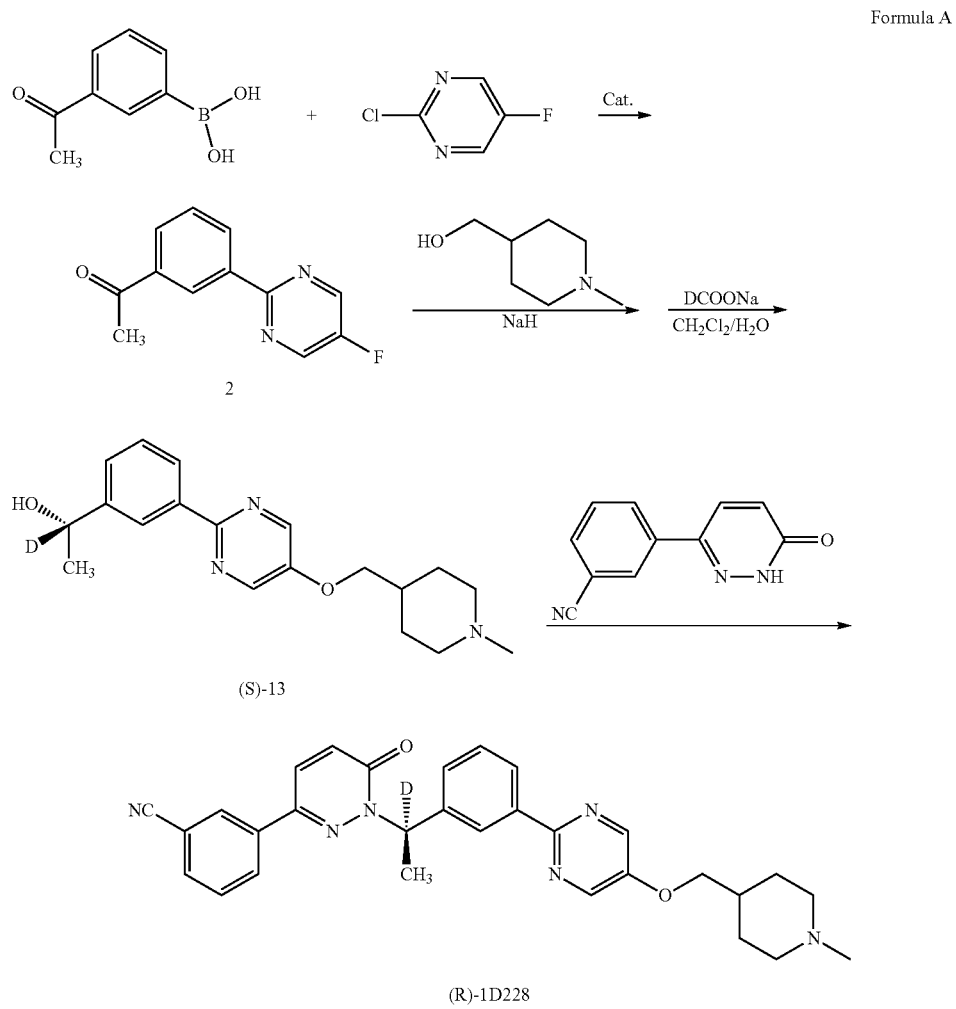

Formula A

The preparation process of (R)-1D288 includes the following steps:
(1) Conducting a chiral hydrogen transfer reaction between the intermediate 8b and deuterated sodium formate in the presence of the catalyst dichloro(p-cymene) ruthenium (II) dimer and the ligand (S,S)-CsDPEN to obtain a deuterated intermediate (S)-13; the structural formula of the intermediate 8b is shown in Formula 13;

Formula 13

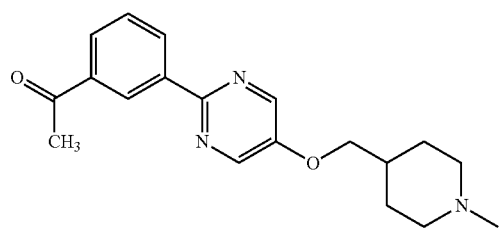

The structural formula of the deuterated intermediate (S)-13 is shown as below:

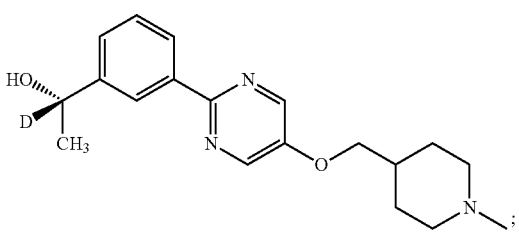

(2) Conducting Mitsunobu reaction between the deuterated intermediate (S)-13 and cyano-carrying pyridazinone to obtain a chiral oxygen-containing deuterated pyrimidine derivative with an inverted configuration, R-configuration.

Wherein, the reagents and reaction conditions for each step are illustrated as below:

Specifically for step (1): the molar ratio of the intermediate 8b, deuterated sodium formate, dichloro(p-cymene)

ruthenium (II) dimer and the ligand (S,S)-CsDPEN is (1.0 to 5.0):(5.0 to 25):(0.05 to 0.25):(0.1 to 0.5), the solvent is dichloromethane and water at a mass ratio of 2:1, the reaction temperature is 25 to 35° C., and the reaction time is 8 to 10 hours; obtaining the deuterated intermediate (S)-13 (its structural formula is shown as (S)-13 in Formula A); the intermediate 8b is prepared by reacting the intermediate 2 with 1-methyl-4-piperidinemethanol in the presence of sodium hydride.

In the present disclosure, the intermediate 8b can also be used in the reaction of step (1) directly without purification, in particular: the intermediate 2 is crosslinked with 1-methylpiperidine-4-methanol in the presence of sodium hydride, the reaction solution is extracted with dichloromethane to obtain a dichloromethane extraction phase; the dichloromethane extraction phase contains the intermediate 8b, which can directly replace the intermediate 8b in step (1) for reaction. When the reaction of step (1) is conducted with dichloromethane extraction phase, the reaction conditions are as below: the molar ratio of the intermediate 2, deuterated sodium formate, dichloro(p-cymene) ruthenium (II) dimer and the ligand (S,S)-CsDPEN is (1.0 to 5.0):(3.0 to 15):(0.005 to 0.10):(0.01 to 0.2), the reaction solvent is dichloromethane and water at a mass ratio of 2:1; the reaction temperature is 25 to 35° C., and the reaction time is 8 to 10 hours, obtaining the deuterated intermediate (S)-13 (its structural formula is shown as (S)-13 in Formula A).

Specifically for Mitsunobu reaction in step (2): Conducting Mitsunobu reaction of the deuterated intermediate (S)-13, 3-(6-oxo-1,6-dihydropyridazin-3-yl)-benzonitrile, triphenylphosphine and diisopropylazodicarboxylate in a solvent, wherein the molar ratio of the deuterated intermediate (S)-13, 3-(6-oxo-1,6-dihydropyridazin-3-yl)-benzonitrile, triphenylphosphine and diisopropylazodicarboxylate is (0.5 to 2.5):(0.5 to 2.5):(0.75 to 3.75):(0.75 to 3.75); the solvent is tetrahydrofuran, firstly reacting at 0 to 4° C. for 15 to 30 minutes, then reacting at 25 to 40° C. for 18 to 24 hours.

The novel pyrimidine derivatives above have excellent inhibitory effects on the proliferation of tumor cells, especially the non-small cell lung cancer cells expressed by c-Met, with the inhibitory activities reaching a level of nanomole.

The present invention further provides pharmaceutically acceptable salts of the novel pyrimidine derivatives, which are corresponding salts formed from the novel pyrimidine derivatives and pharmaceutically acceptable anions by well-known salt-forming processes.

A use of the novel pyrimidine derivatives in the preparation of anti-tumor drugs, in which the novel pyrimidine derivatives are used as active ingredients to treat tumors effectively; preferably the novel pyrimidine derivatives are chiral derivatives, more preferably optical chiral isomers in R-configuration; most preferably optical chiral deuterated isomers in R-configuration.

The novel pyrimidine derivatives are used in the form of pharmaceutical solvates, and the solvates are preferably hydrates.

The present invention further provides a pharmaceutical composition for treating tumors, comprising effective amount of the novel pyrimidine derivatives and pharmaceutically acceptable adjuvants. The pharmaceutical composition can be made into injections, tablets, capsules, pills, suspensions, or emulsions for use; its administration routes may be oral administration, transdermal, intravenous or intramuscular injection.

Compared with the prior art, the present invention has the following benefits and effects:

(1) The introduction of a chiral structure in the molecule of the invention has good effects on its bioavailability and anti-tumor activity.

(2) The introduction of an isotope of hydrogen (deuterium) at the sites that are prone to metabolism in the molecule of the invention is beneficial to improve the pharmacokinetic properties of such anti-tumor compounds and enhance their efficacy and bioavailability due to that the carbon-deuterium bond is more stable than the carbon-hydrogen bond.

(3) The introduction of atoms or groups such as sulfur, selenium and sulfoxide in the molecule of the invention makes it have different pharmacological properties, which has good effects for researching other adaptabilities of such compounds.

(4) It is demonstrated through the tests on anti-tumor activity at the cellular level that the compounds of the invention have excellent anti-tumor activities.

(5) It is demonstrated through the metabolism stability tests of the compounds of the invention in liver microsomes that the stabilities of the anti-tumor compounds are significantly improved by the introduction of the isotope of hydrogen (deuterium).

(6) The synthetic steps of the resulting compound (R)-1D228 in the disclosure are less than the steps for preparing a compound containing four deuterium, in which there is no need for a step of preparing the deuterated acetyl intermediate, this process is simple and can be used for large-scale preparation.

(7) Compared with the preparation of the compound containing four deuterium, the preparation of the resulting compound (R)-1D228 in the disclosure avoids the use of expensive deuterated chloroform and deuterated methanol, thus greatly reducing the cost.

(8) It is demonstrated from animal experiments in vitro and in vivo that the resulting compound (R)-1D228 in the disclosure has excellent anti-tumor activity, the anti-tumor rate of which is significantly higher than that of the positive drug Tepotinib, and slightly higher than that of the compound (R)-4D228 containing four deuterium in the prior art.

DESCRIPTION OF THE EMBODIMENTS

Figure 1:
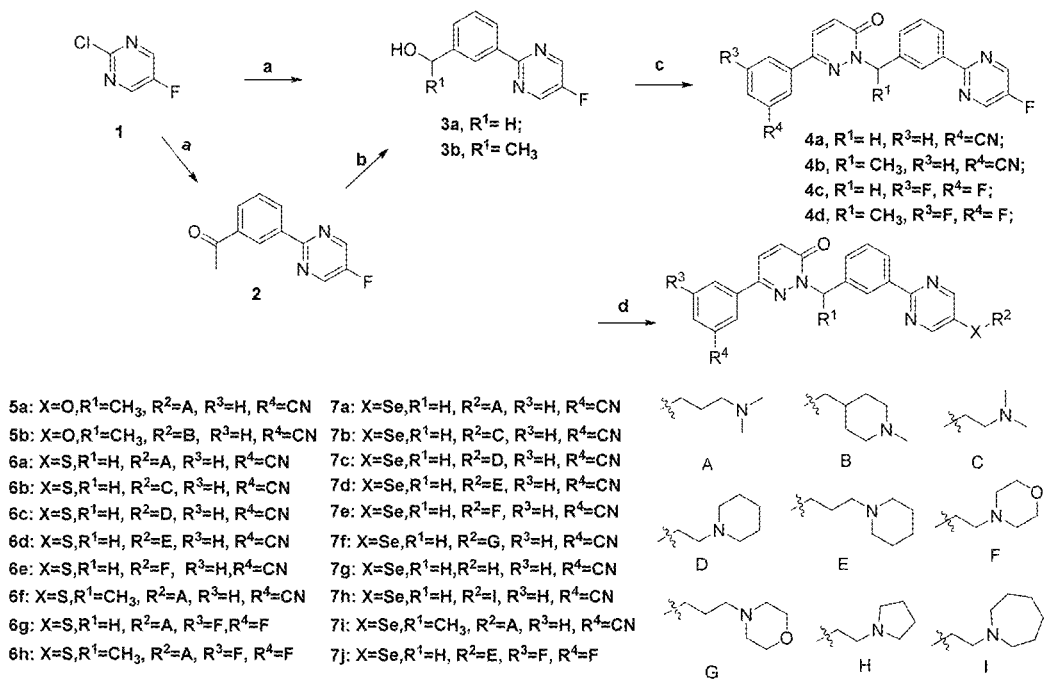
FIG. 1 is the synthesis route of achiral or racemic pyrimidine derivatives 5, 6, 7.
Figure 2:
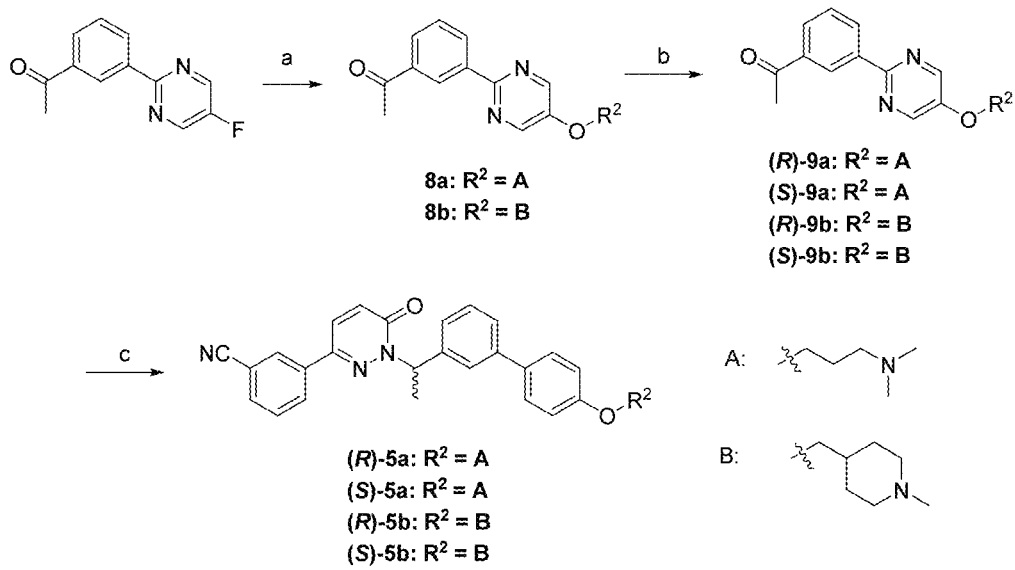
FIG. 2 is the synthesis route of chiral pyrimidine derivative 5 in R-configuration or S-configuration.
Figure 3:
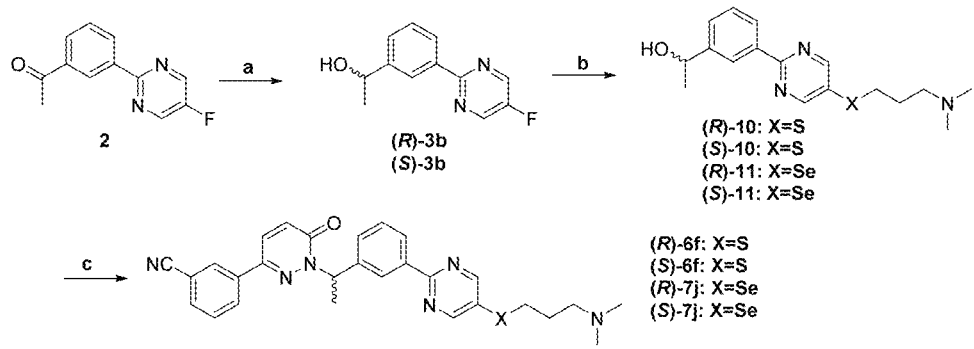
FIG. 3 is the synthesis route of chiral pyrimidine derivatives 6f and 7j in R-configuration or S-configuration.
Figure 4:
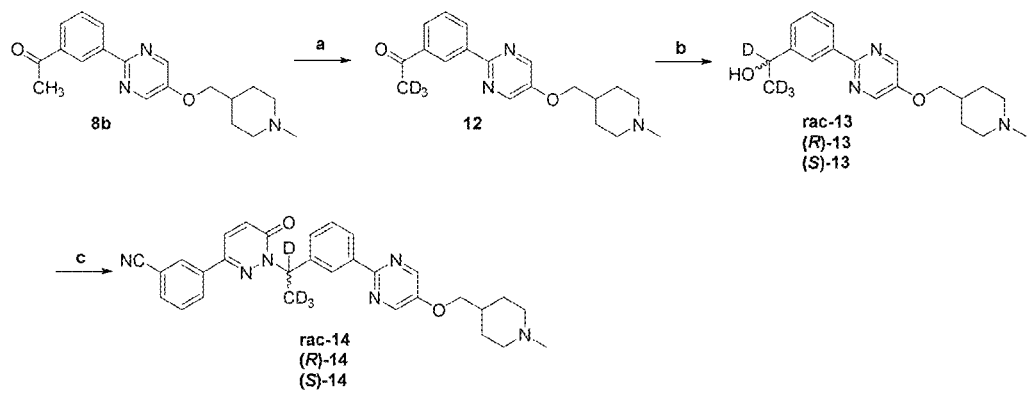
FIG. 4 is the synthesis route of chiral oxygen-containing deuterated pyrimidine derivative 14 in R-configuration or S-configuration.
Figure 5:
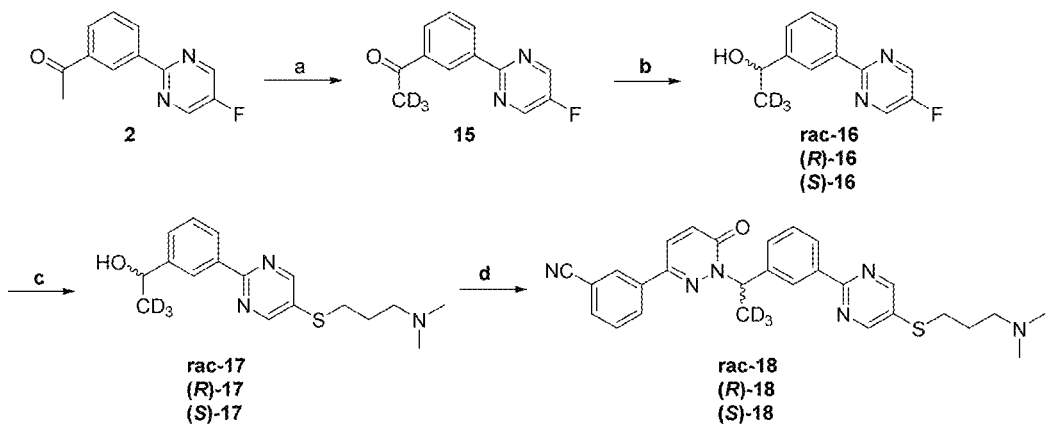
FIG. 5 is the synthesis route of chiral oxygen-containing deuterated pyrimidine derivative 18 in R-configuration or S-configuration.

The present invention will be further described in detail in combination with the following embodiments, but the implementation of the invention is not limited thereto.

Embodiment 1: Anti-Tumor Compound (±)-5b

Anti-tumor compound (±)-5b, the structural formula of which is as shown below, and the synthesis steps of which are as below:

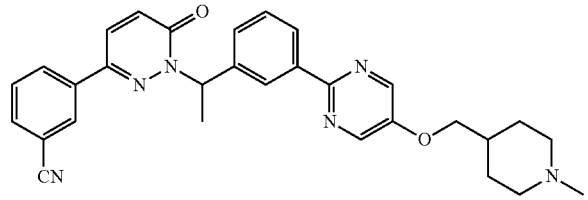

Structrual formula of compound (±)-5b

Preparation of intermediate 2: An aqueous solution (32 mL water) of sodium carbonate (66 mmol) were added to a solution of 5-fluoro-2-chloropyrimidine (33 mmol) in toluene (32 mL) and bis(triphenyl phosphine) palladium chloride (0.33 mmol), then added to a solution of acetyl phenylboronic acid (32 mmol) in ethanol (65 mL) dropwise. The reaction was stirred at 80° C. under the protection of nitrogen for 18 hours, cooled to room temperature, and filtrated. The filtrates were added into ethyl acetate and water, the organic phase was separated, dried over anhydrous sodium sulfate. The crude product was separated by silica gel column chromatography (ethyl acetate:petroleum ether, 8:1) to get a light yellow solid, i.e., the intermediate 2. Yield: 61%. $^1$H NMR (400 MHz, CDCl$_3$) δ 8.98 (t, J=1.6 Hz, 1H), 8.70 (s, 2H), 8.59 (s, 1H), 8.09 (s, 1H), 7.60 (s, 1H), 2.71 (s, 3H).

Preparation of intermediate 3b: At 0° C., sodium borohydride (15 mmol) was added to a suspension of intermediate 2 (10 mmol) in absolute ethyl alcohol/tetrahydrofuran batchwise. After stirring at 0° C. for 1 hour, the ice bath is removed. After stirring at room temperature for 1 hour, water was slowly added into the reaction solution to quench the reaction. The mixture was extracted with ethyl acetate for three times. The organic layer was washed with saturated sodium chloride solution, dried over anhydrous sodium sulfate, and rotary evaporated to get a crude product. The crude product was purified by column chromatography to obtain a white solid, i.e., the intermediate 3b (ethyl acetate:petroleum=4:1), yield: 83%. $^1$H NMR (500 MHz, CDCl$_3$) δ 8.65 (s, 2H), 8.38 (s, 1H), 8.28 (d, J=7.5 Hz, 1H), 7.52 (d, J=7.5 Hz, 1H), 7.47 (t, J=7.6 Hz, 1H), 5.01 (dd, J=6.0, 3.0 Hz, 1H), 1.56 (d, J=6.4 Hz, 3H).

Synthesis of intermediate 4b: The intermediate 3b (5 mmol) was added batchwise into sulfoxide chloride (25 mmol) with stirring, and reacted at 30° C. for 2 hours. Excessive sulfoxide chloride was removed under reduced pressure. The residues were added into toluene and stirred. Toluene was removed under reduced pressure to get a chlorinated intermediate. The chlorinated intermediate and potassium carbonate (7.5 mmol) were added into a solution of 3-(6-oxo-1,6-dihydropyridazin-3-yl)-benzonitrile (6 mmol) in N-methyl pyrrolidinone, stirred at 80° C. to react for 20 hours. The reaction was quenched with water, extracted with ethyl acetate for 3 times. The organic phase was washed with saturated saline, and dried over anhydrous sodium sulfate. The solvent was removed under reduced pressure. The crude product was separated by silica gel column chromatography (dichloromethane:methanol=100:1) to get a yellow solid, i.e., the intermediate 4b, yield: 68%. $^1$H NMR (400 MHz, CDCl$_3$) δ 8.70 (s, 3H), 8.33 (d, J=7.8 Hz, 1H), 8.19 (s, 1H), 7.98 (d, J=8.0 Hz, 1H), 7.70 (d, J=7.7 Hz, 1H), 7.66-7.52 (m, 3H), 7.46 (t, J=7.7 Hz, 1H), 7.04 (d, J=9.7 Hz, 1H), 6.56 (q, J=7.0 Hz, 1H), 1.93 (d, J=7.1 Hz, 3H).

Synthesis of target (±)-5b: At 0° C., sodium hydride (60%, 1.5 mmol) was added batchwise into a solution of 1-methyl piperidine-4-methanol (1.2 mmol) in N,N-dimethyl formamide, and stirred for 15 minutes. The intermediate 4b was then added into the reaction solution slowly at 0° C., warmed to room temperature slowly and stirred for 1 hour. The reaction was quenched with water, and extracted with ethyl acetate. The combined organic layer was dried, and concentrated. The crude product was purified by silica-gel column chromatography (dichloromethane:methanol=20:1) to obtain light yellow oil, i.e., the target (±)-5b, yield: 69%.

$^1$H NMR (400 MHz, CDCl$_3$) δ 8.67 (s, 1H), 8.49 (s, 2H), 8.28 (d, J=7.8 Hz, 1H), 8.20 (s, 1H), 7.97 (d, J=8.0 Hz, 1H), 7.68 (d, J=7.7 Hz, 1H), 7.61-7.50 (m, 3H), 7.42 (t, J=7.7 Hz, 1H), 7.02 (d, J=9.7 Hz, 1H), 6.54 (q, J=7.0 Hz, 1H), 3.96 (d, J=5.9 Hz, 2H), 2.94 (d, J=11.5 Hz, 2H), 2.31 (s, 3H), 1.99 (d, J=10.2 Hz, 2H), 1.91 (d, J=7.0 Hz, 3H), 1.85 (m, 3H), 1.50 (dd, J=18.4, 8.6 Hz, 2H). 13C NMR (101 MHz, CDCl$_3$) δ 159.22, 157.76, 151.21, 144.04, 141.88, 140.66, 137.72, 136.40, 132.46, 130.29, 129.82, 129.79, 129.74, 129.69, 128.79, 128.71, 127.30, 126.98, 118.70, 113.38, 71.78, 56.23, 54.19, 43.99, 33.64, 26.06, 20.12. HRMS (ESI) m/z calculated C$_{30}$H$_{31}$N$_6$O$_2$ [M+H]$^+$, 507.2508; found, 507, 2519. HPLC purity: 95.2%, retention time: 16.68 min.

Compound (±)-5a was prepared with a similar method.

Embodiment 2: Anti-Tumor Compound 6a

Anti-tumor compound 6a, the structural formula of which is as shown below, and the synthesis steps of which are as below:

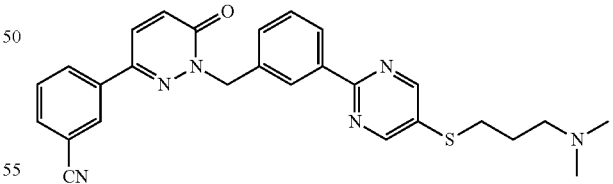

Structural formula of compound 6a

Preparation of intermediate 3a: Into an aqueous solution (32 mL) of sodium carbonate (66 mmol) were added a solution of 5-fluoro-2-chloropyrimidine (33 mmol) in toluene (32 mL) and bis(triphenyl phosphine) palladium dichloride (0.33 mmol), then added a solution of hydroxymethyl phenyl boronic acid (32 mmol) in ethanol (65 mL). The reaction was stirred at 80° C. under the protection of nitrogen for 18 hours, cooled to room temperature, and filtrated.

Into the filtrate were added ethyl acetate and water. The organic phase was separated, and dried over anhydrous sodium sulfate. The crude product was separated by silica gel column chromatography (ethyl acetate:petroleum ether, 8:1) to get a light yellow solid, i.e., the intermediate 3a. Yield: 61%. $^1$H NMR (400 MHz, CDCl$_3$) δ 8.66 (d, J=1.8 Hz, 1H), 8.37 (d, J=4.9 Hz, 1H), 8.31 (s, 1H), 7.54-7.46 (m, 3H), 4.80 (s, 1H), 1.99 (s, 1H).

Preparation of intermediate 4a: The intermediate 3a (5 mmol) was added into sulfoxide chloride (25 mol) batchwise with stirring, and reacted at 25° C. for 2 hours. Excessive sulfoxide chloride was removed under reduced pressure. The residues were added into toluene. Toluene was removed under reduced pressure to get a chloride as the crude product. The crude product and potassium carbonate (2.75 mol) were added into a solution of 3-(6-oxo-1,6-dihydro-pyridazin-3-yl)-benzonitrile in N,N-dimethyl formamide, and stirred at 80° C. to react for 20 hours. The reaction was quenched with water, extracted with ethyl acetate for 3 times. The organic phase was washed with saturated saline, dried over anhydrous sodium sulfate. The solvent was removed under reduced pressure. The crude product was separated by silica gel column chromatography (dichloromethane:methanol: 100:1) to get a yellow solid, i.e., the intermediate 4a, yield: 68%. $^1$H NMR (500 MHz, CDCl$_3$) δ 8.68 (s, 2H), 8.60 (s, 1H), 8.34 (d, J=7.8 Hz, 1H), 8.16 (s, 1H), 7.99 (d, J=8.0 Hz, 1H), 7.70 (d, J=7.7 Hz, 1H), 7.65 (d, J=9.7 Hz, 1H), 7.62-7.55 (m, 2H), 7.48 (t, J=7.7 Hz, 1H), 7.09 (s, 1H), 5.51 (s, 2H).

Synthesis of target 6a: N,N-dimethylamino chloropropane hydrochloride (2 mmol) and thiourea (2 mmol) are dissolved in absolute ethyl alcohol (50 mL), refluxed for 7 hours under the protection of nitrogen, cooled to room temperature, and rotary evaporated under reduced pressure to remove the solvent, thus obtaining isothiourea analogue, which was directly used in the following step without further purification. The intermediate 4a (1 mmol), isothiourea analogue (2 mmol) and sodium hydroxide solid (4 mmol) were placed in a single-port flask, with the nitrogen being replaced, into which were then added N,N-dimethyl formamide/water=5: 1, stirred at room temperature for 15 minutes, then stirred at 60° C. for 3 hours. Upon the completion of the reaction, the reaction solution was diluted with ethyl acetate, washed with water and brine, rotary evaporated and concentrated. The crude product was purified by column chromatography (CH$_2$Cl$_2$:CH$_3$OH=20:1) to obtain a yellow oil, i.e., the target 6a, yield: 56%. $^1$H NMR (400 MHz, CDCl$_3$) δ 8.77 (s, 2H), 8.62 (s, 1H), 8.36 (d, J=7.8 Hz, 1H), 8.16 (s, 1H), 8.00 (d, J=8.1 Hz, 1H), 7.69 (s, 1H), 7.65 (d, J=9.7 Hz, 1H), 7.58 (dd, J=14.7, 7.0 Hz, 2H), 7.47 (t, J=7.7 Hz, 1H), 7.08 (d, J=9.7 Hz, 1H), 5.51 (s, 2H), 3.03 (t, J=7.3 Hz, 2H), 2.41 (t, J=7.0 Hz, 2H), 2.22 (s, 6H), 1.83 (dt, J=14.1, 7.1 Hz, 4H). $^{13}$C NMR (101 MHz, CDCl$_3$) δ 161.75, 159.45, 157.63, 142.21, 137.56, 136.25, 135.96, 132.58, 131.26, 130.85, 130.33, 129.93, 129.82, 129.71, 129.42, 129.11, 128.73, 127.81, 118.44, 113.39, 57.96, 55.49, 45.42, 31.75, 27.16. HRMS (ESI) m/z C$_{27}$H$_{26}$N$_6$OS [M+H]$^+$, calculated 483.1962; found 483.1947. HPLC purity: 96.8%, retention time: 9.65 min.

Compounds 6b-6h, 7a-7j were prepared with a similar method.

Embodiment 3: Anti-Tumor Compound (R)-5b

Anti-tumor compound (R)-5b, the structural formula of which is as shown below, and the synthesis steps of which are as below:

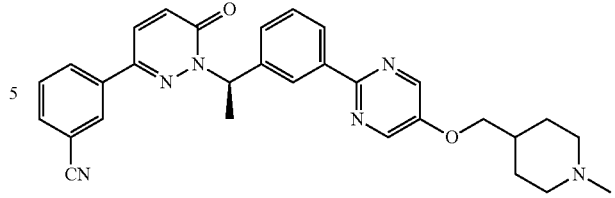

Structural formula of compound (R)-5b

Preparation of intermediate 8b: At 0° C., sodium hydride (60%, 1.5 mmol) was added into a solution of 1-methyl piperidine-4-methanol (1.2 mmol) in N,N-dimethyl formamide (10 mL) batchwise, and stirred for 15 minutes. The intermediate 2 was then slowly added into the mixture at 0° C. The reaction mixture was warmed to room temperature slowly and stirred for 1 hour. The reaction solution was washed with water, and extracted with ethyl acetate. The combined organic layer was dried, rotary evaporated to obtain a crude product. The crude product was purified by silica-gel column chromatography (dichloromethane:methanol=20:1) to obtain light yellow oil, i.e., the intermediate 8b, yield: 73%. $^1$H NMR (400 MHz, CDCl$_3$) δ 8.93 (t, J=1.5 Hz, 1H), 8.56 (dt, J=7.8, 1.3 Hz, 1H), 8.47 (s, 2H), 8.04 (dt, J=7.7, 1.3 Hz, 1H), 7.57 (t, J=7.8 Hz, 1H), 3.97 (d, J=5.8 Hz, 2H), 2.93 (d, J=11.0 Hz, 2H), 2.70 (s, 3H), 2.31 (s, 3H), 2.06-1.91 (m, 4H), 1.88 (d, J=2.6 Hz, 1H), 1.48 (qd, J=13.6, 13.1, 3.6 Hz, 2H).

Preparation of intermediate (S)-9b: Dichloro(p-cymene) ruthenium (II) dimer (0.01 mmol) and a chiral ligand (S,S)-CsDPEN (0.02 mmol) were placed in a 50 mL single-port flask, into which was added pure water (5 mL), and stirred at 40° C. for 4 hours under the protection of nitrogen. After then, the intermediate 8b (1 mmol, dissolved in 8 mL dichloromethane) and sodium formate (5 mmol, dissolved in 3 mL pure water) were promptly added, and stirred at room temperature for 10 hours. Upon the completion of the reaction, 10 mL water was added into the reaction system. The water phase was extracted with dichloromethane. The combined organic layer was dried and concentrated. The crude product was purified by silica-gel column chromatography (dichloromethane:methanol=20:1) to obtain light yellow oil, i.e., the intermediate (S)-9b, yield: 70%. $^1$H NMR (400 MHz, CDCl$_3$) δ 8.44 (s, 2H), 8.34 (s, 1H), 8.24 (d, J=7.1 Hz, 1H), 7.53-7.42 (m, 2H), 4.99 (q, J=6.4 Hz, 1H), 4.12 (t, J=6.3 Hz, 2H), 2.45 (t, J=7.2 Hz, 2H), 2.25 (s, 6H), 2.02-1.94 (m, 2H), 1.55 (d, J=6.4 Hz, 3H). 98.0% ee, Daicel AD column (0.46×25 cm), n-hexane/isopropanol=75/25, 0.5 mL/min, λ=254 nm, t$_R$=15.79 (R), t$_S$=18.85 (S).

Synthesis of the target (R)-5b: At 0° C., diisopropyl azodicarboxylate (0.600 mmol, dissolved in 1 mL N,N-dimethyl formamide) was slowly added into a solution of 3-(6-oxo-1,6-dihydropyridazin-3-yl)-benzonitrile (0.40 mmol), the intermediate (S)-9b (0.40 mmol) and triphenyl phosphine (0.60 mmol) in tetrahydrofuran (4 mL), warmed to room temperature slowly under the protection of nitrogen, stirred at room temperature for 18 hours, and rotary evaporated under reduced pressure to remove the solvent. The crude product was purified by silica-gel column chromatography (dichloromethane/methanol=20:1) to obtain a colorless oil, i.e., the target (R)-5b, yield: 57%. $^1$H NMR (400 MHz, CDCl3) δ 8.67 (s, 1H), 8.49 (s, 2H), 8.28 (d, J=7.8 Hz, 1H), 8.20 (s, 1H), 7.97 (d, J=8.0 Hz, 1H), 7.68 (d, J=7.7 Hz, 1H), 7.61-7.50 (m, 3H), 7.42 (t, J=7.7 Hz, 1H), 7.02 (d, J=9.7 Hz, 1H), 6.54 (q, J=7.0 Hz, 1H), 3.96 (d, J=5.9 Hz, 2H), 2.94 (d, J=11.5 Hz, 2H), 2.31 (s, 3H), 1.99 (d, J=10.2 Hz, 2H), 1.91 (d, J=7.0 Hz, 3H), 1.85 (m, 3H), 1.50 (dd, J=18.4, 8.6 Hz, 2H). $^{13}$C NMR (101 MHz, CDCl3) δ 159.22, 157.76, 151.21, 144.04, 141.88, 140.66, 137.72, 136.40, 132.46, 130.29, 129.82, 129.79, 129.74, 129.69, 128.79, 128.71, 127.30, 126.98, 118.70, 113.38, 71.78, 56.23, 54.19, 43.99, 33.64, 26.06, 20.12. HRMS (ESI) m/z calculated $C_{30}H_{31}N_6O_2$ [M+H]$^+$, 507.2508; found, 507,2519. HPLC purity: 95.8%, retention time: 16.71 min.

Compounds (S)-5b, (R)-5a and (S)-5a were prepared with a similar method.

Embodiment 4: Anti-Tumor Compound (R)-6f

Anti-tumor compound (R)-6f, the structural formula of which is as shown below, and the synthesis steps of which are as below:

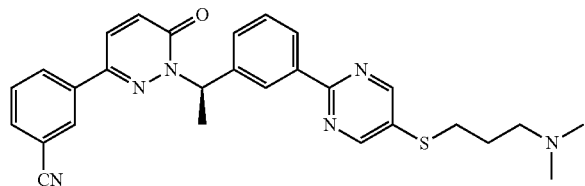

Structural formula of compound (R)-6f

Preparation of intermediate (S)-3b: Dichloro(p-cymene) ruthenium (II) dimer (0.05 mmol) and a chiral ligand (S,S)-CsDPEN (0.10 mmol) were placed in a 100 mL single-port flask, into which was added pure water (25 mL), and stirred at 40° C. under the protection of nitrogen for 4 hours. After then, the intermediate 2 (5 mmol, dissolved in 40 mL dichloromethane) and sodium formate (25 mmol, dissolved in 15 mL pure water) were promptly added, and stirred at room temperature for 10 hours. Upon the completion of the reaction, 30 mL water was added into the reaction system. The water phase was extracted with dichloromethane. The combined organic layer was dried and concentrated. The crude product was purified by silica-gel column chromatography (petroleum ether:ethyl acetate=2:1) to obtain a white solid, i.e., the intermediate (S)-3b, yield: 71%. $^1$H NMR (500 MHz, CDCl$_3$) δ 8.65 (s, 2H), 8.38 (s, 1H), 8.28 (d, J=7.5 Hz, 1H), 7.52 (d, J=7.5 Hz, 1H), 7.47 (t, J=7.6 Hz, 1H), 5.01 (dd, J=6.0, 3.0 Hz, 1H), 1.56 (d, J=6.4 Hz, 3H). $[\alpha]_D^{20}$=−32.5 (c=0.1 g/100 mL, CH$_3$OH). 97.1% ee. Daicel OD column (0.46×25 cm), n-hexane/isopropanol=85/15, 0.5 mL/min, λ=254 nm, $t_R$=13.98 (R), $t_S$=14.95 (S).

Preparation of intermediate (S)-11a: N,N-dimethylamino chloropropane hydrochloride (1 mmol) and thiourea (1 mmol) in absolute ethyl alcohol (50 mL) were refluxed for 7 hours under the protection of nitrogen, cooled to room temperature, rotary evaporated under reduced pressure to remove the solvent, thus obtaining an isothiourea analogue, which was directly used in the following step without further purification. The intermediate (S)-3b (1 mmol), the isothiourea analogue (2 mmol) and sodium hydroxide (4 mmol) were placed in a single-port flask, the air in which was replaced with nitrogen, and then into which was added N,N-dimethyl formamide/water=5:1, stirred at room temperature for 15 minutes, and then stirred at 60° C. for 3 hours. Upon the completion of the reaction, the reaction solution was diluted with ethyl acetate, washed with water and brine, rotary evaporated and concentrated. The crude product was purified by column chromatography (dichloromethane:methanol=20:1) to obtain a colorless oil, i.e., the intermediate (S)-11a, yield: 56%. $^1$H NMR (400 MHz, CDCl$_3$) δ 8.75 (s, 2H), 8.40 (q, J=1.2, 0.7 Hz, 1H), 8.32 (dt, J=7.6, 1.6 Hz, 1H), 7.58-7.44 (m, 2H), 5.01 (q, J=6.4 Hz, 1H), 3.08-2.97 (m, 2H), 2.39 (t, J=7.0 Hz, 2H), 2.21 (s, 6H), 1.85-1.78 (m, 2H), 1.56 (d, J=6.5 Hz, 3H).

Synthesis of target (R)-6f: At 0° C., diisopropyl azodicarboxylate (0.60 mmol, dissolved in 1 mL N,N-dimethyl formamide) was slowly added into a solution of 3-(6-oxo-1,6-dihydropyridazin-3-yl)-benzonitrile (0.40 mmol), the compound (S)-11a (0.40 mmol) and triphenyl phosphine (0.60 mmol) in tetrahydrofuran (4 mL), warmed to room temperature slowly under the protection of nitrogen, and stirred at room temperature for 18 hours. The solvent was removed by rotary evaporation under reduced pressure. The crude product was purified by silica-gel column chromatography (dichloromethane/methanol=20:1) to obtain light yellow oil, i.e., the target (R)-6f, yield: 56%. $^1$H NMR (500 MHz, CDCl$_3$) δ 8.81 (s, 2H), 8.76 (s, 1H), 8.36 (d, J=7.9 Hz, 1H), 8.23 (s, 1H), 7.97 (d, J=8.0 Hz, 1H), 7.70 (d, J=7.8 Hz, 1H), 7.59 (dt, J=12.6, 8.8 Hz, 3H), 7.46 (t, J=7.7 Hz, 1H), 7.04 (d, J=9.7 Hz, 1H), 6.55 (d, J=7.0 Hz, 1H), 3.07 (t, J=7.1 Hz, 2H), 2.73-2.62 (m, 2H), 2.43 (s, 6H), 1.98 (dd, J=14.4, 7.2 Hz, 2H), 1.92 (d, J=7.1 Hz, 3H). $^{13}$C NMR (126 MHz, CDCl$_3$) δ 162.05, 159.23, 157.94, 141.86, 140.79, 137.37, 136.30, 132.46, 130.49, 130.31, 129.83, 129.79, 129.72, 128.89, 128.75, 127.75, 127.40, 118.64, 113.33, 57.40, 56.24, 44.56, 31.58, 26.04, 20.06. IRMS (ESI) m/z $C_{28}H_{28}N_6OS$ [M+H]$^+$, calculated 497.2118; found 497.2111. HPLC purity: 99.0%, retention time: 17.24 min. 90.7% ee. Daicel OD column (0.46×25 cm), n-hexane/ethanol=80/20, 0.5 mL/min, k=254 nm, $t_R$=29.94 (R), $t_S$=31.88 (S).

Compounds (S)-6f, (R)-7j and (S)-7j were prepared with a similar method.

Embodiment 5: Anti-Tumor Compound (R)-14

Anti-tumor compound (R)-14, the structural formula of which is as shown below, and the synthesis steps of which are as below:

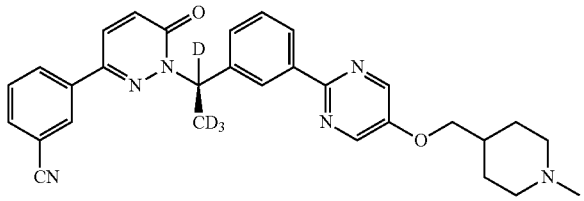

Structural formula of compound (R)-14

Preparation of intermediate 12: 1,5,7 triazabicyclo[4.4.0]dec-5-ene (TBD, 0.5 mmol) was added into a solution of the intermediate 8b (5 mmol) in deuterated chloroform (30 mL), stirred at room temperature for 12 hours, and rotary evaporated to get a crude product. The crude product was purified by column chromatography (dichloromethane:methanol=50:1) to obtain an intermediate 12. $^1$H NMR (400 MHz, CDCl$_3$) δ 8.93 (t, J=1.5 Hz, 1H), 8.56 (dt, J=7.8, 1.3 Hz, 1H), 8.47 (s, 2H), 8.04 (dt, J=7.7, 1.3 Hz, 1H), 7.57 (t, J=7.8 Hz, 1H), 3.97 (d, J=5.8 Hz, 2H), 2.93 (d, J=11.0 Hz, 2H), 2.70 (s, 3H), 2.06-1.91 (m, 4H), 1.88 (d, J=2.6 Hz, 1H), 1.48 (qd, J=13.6, 13.1, 3.6 Hz, 2H).

Preparation of intermediate (S)-13: Dichloro(p-cymene) ruthenium (II) dimer (0.01 mmol) and a chiral ligand (S,S)-CsDPEN (0.05 mmol) were placed in a 50 mL single-port flask, into which was added heavy water (3 mL), and stirred at 40° C. under the protection of nitrogen for 4 hours. After then, the intermediate 12 (1 mmol, dissolved in 8 mL deuterated chloroform) and deuterated sodium formate (5 mmol, dissolved in 3 mL heavy water) were added promptly, and stirred at room temperature for 10 hours. Upon the completion of the reaction, 10 mL water was added into the reaction system. The water phase was extracted with dichloromethane. The combined organic layer was dried and concentrated. The crude product was recrystallized with ethyl acetate to obtain a white solid, i.e., the intermediate (S)-13, yield: 70%. $^1$H NMR (400 MHz, CDCl$_3$) δ 8.44 (s, 2H), 8.34 (dd, J=1.9, 1.4 Hz, 1H), 8.27-8.23 (m, 1H), 7.50-7.44 (m, 2H), 3.92 (d, J=5.9 Hz, 2H), 2.91 (d, J=11.4 Hz, 2H), 2.29 (s, 3H), 2.00-1.93 (m, 2H), 1.87-1.81 (m, 3H), 1.47-1.35 (m, 2H).

Synthesis of target (R)-14: At 0° C., diisopropyl azodicarboxylate (0.60 mmol, dissolved in 1 mL N,N-dimethyl formamide) was slowly added into a solution of 3-(6-oxo-1,6-dihydropyridazin-3-yl)-benzonitrile (0.40 mmol), the compound (S)-13 (0.40 mmol) and triphenyl phosphine (0.60 mmol) in tetrahydrofuran (4 mL), warmed to room temperature slowly under the protection of nitrogen, and stirred at room temperature for 18 hours. The solvent was removed by rotary evaporation under reduced pressure. The crude product was purified by silica-gel column chromatography (dichloromethane/methanol=20:1) to obtain light yellow oil, i.e., the target (R)-14, yield: 56%. $^1$H NMR (400 MHz, Chloroform-d) δ 8.67 (t, J=1.6 Hz, 1H), 8.50 (s, 2H), 8.28 (dt, J=7.8, 1.4 Hz, 1H), 8.21 (t, J=1.5 Hz, 1H), 7.98 (dt, J=8.0, 1.2 Hz, 1H), 7.69 (m, 1H), 7.60-7.50 (m, 3H), 7.43 (t, J=7.7 Hz, 1H), 7.02 (d, J=9.7 Hz, 1H), 3.96 (d, J=6.0 Hz, 2H), 2.94 (d, J=11.5 Hz, 2H), 2.31 (s, 3H), 2.05-1.94 (m, 2H), 1.90-1.83 (m, 3H), 1.48 (qd, J=12.9, 3.5 Hz, 2H). $^{13}$C NMR (101 MHz, CDCl$_3$) δ 159.28, 157.28, 151.67, 143.93, 141.84, 140.56, 137.85, 136.34, 132.45, 130.29, 129.85, 129.75, 129.65, 129.35, 128.78, 128.70, 127.23, 126.95, 118.61, 113.37, 73.27, 55.24, 46.33, 35.19, 29.71, 28.80, 19.92. HRMS (ESI) m/z C$_{30}$H$_{27}$D$_4$N$_6$O$_2$[M+H]$^+$, calculated 511.2724; found 511.2714. HPLC purity: 99.0%, retention time: 15.03 min. 97.1% ee. Daicel AD column (0.46×25 cm), n-hexane/ethanol=80/20, 0.5 mL/min, λ=254 nm, t$_R$=40.66 (R), t$_S$=64.22 (S).

Compound (S)-14 was prepared with a similar method.

Embodiment 6: Anti-Tumor Compound (R)-18

Anti-tumor compound (R)-18, the structural formula of which is as shown below, and the synthesis steps of which are as below:

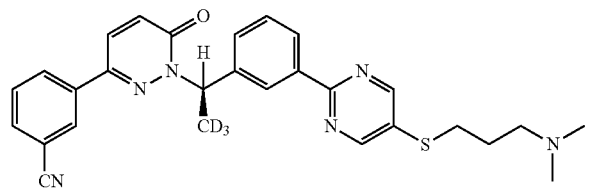

Structural formula of compound (R)-18

Preparation of intermediate 15: 1,5,7-triazabicyclo[4.4.0]dec-5-ene (TBD, 0.5 mmol) was added into a solution of the intermediate 2 (5 mmol) in deuterated chloroform (30 mL), and stirred at room temperature for 12 hours. The organic layer was washed with water, dried over a saturated sodium chloride solution and anhydrous sodium sulfate, and rotary evaporated to obtain a crude product. The crude product was purified by column chromatography (dichloromethane:methanol=50:1) to obtain the desired compound 15. $^1$H NMR (400 MHz, CDCl$_3$) δ 8.98 (t, J=1.6 Hz, 1H), 8.70 (s, 2H), 8.60 (dt, J=7.8, 1.5 Hz, 1H), 8.10 (dt, J=7.7, 1.5 Hz, 1H), 7.60 (t, J=7.8 Hz, 1H), 2.71 (s, 3H).

Preparation of intermediate (S)-16: Dichloro(p-cymene) ruthenium (II) dimer (0.05 mmol) and a chiral ligand (S,S)-CsDPEN (0.10 mmol) were placed in a 100 mL single-port flask, into which was added pure water (25 mL), and stirred at 40° C. under the protection of nitrogen for 4 hours. After then, the intermediate 15 (5 mmol, dissolved in 40 mL dichloromethane) and sodium formate (25 mmol, dissolved in 15 mL pure water) were added promptly, and stirred at room temperature for 10 hours. Upon the completion of the reaction, 30 mL water was added into the reaction system. The water phase was extracted with dichloromethane. The combined organic layer was dried and concentrated. The crude product was purified by silica-gel column chromatography (petroleum ether: ethyl acetate=2:1) to obtain a white solid, i.e., the intermediate (S)-16, yield: 71%. $^1$H NMR (400 MHz, CDCl$_3$) δ 8.73 (s, 2H), 8.40 (t, J=1.8 Hz, 1H), 8.30 (dt, J=7.6, 1.6 Hz, 1H), 7.55-7.43 (m, 2H), 4.98 (s, 1H), 2.99 (t, J=7.3 Hz, 2H), 2.37 (t, J=7.1 Hz, 2H), 2.19 (s, 6H), 1.81 (q, J=7.2 Hz, 2H).

Preparation of intermediate (S)-17: N,N-dimethylamino chloropropane hydrochloride (1 mmol) and thiourea (1 mmol) in absolute ethyl alcohol (50 mL) were refluxed under the protection of nitrogen for 7 hours, and cooled to room temperature. The solvent was removed by rotary evaporation under reduced pressure to obtain an isothiourea analogue, which was directly used in the following step without further purification. The intermediate (S)-16 (1 mmol), the isothiourea analogue (2 mmol) and sodium hydroxide (4 mmol) were placed in a single-port flask, the air in which was replaced with nitrogen, and then into which was added N,N-dimethyl formamide/water=5:1, stirred at room temperature for 15 minutes, and then stirred at 60° C. for 3 hours. Upon the completion of the reaction, the reaction solution was diluted with ethyl acetate, washed with water and brine, rotary evaporated and concentrated. The crude product was purified by column chromatography (dichloromethane:methanol=20:1) to obtain colorless oil, i.e., the intermediate (S)-17, yield: 56%. $^1$H NMR (400 MHz, CDCl$_3$) δ 8.75 (s, 2H), 8.40 (q, J=1.2, 0.7 Hz, 1H), 8.32 (dt, J=7.6, 1.6 Hz, 1H), 7.58-7.44 (m, 2H), 5.01 (s, 1H), 3.08-2.97 (m, 2H), 2.39 (t, J=7.0 Hz, 2H), 2.21 (s, 6H), 1.85-1.78 (m, 2H).

Synthesis of target (R)-18: At 0° C., diisopropyl azodicarboxylate (0.60 mmol, dissolved in 1 mL N,N-dimethyl formamide) was slowly added into a solution of 3-(6-oxo-1,6-dihydropyridazin-3-yl)-benzonitrile (0.40 mmol), the compound (S)-17 (0.40 mmol) and triphenyl phosphine (0.60 mmol) in tetrahydrofuran (4 mL), warmed to room temperature slowly under the protection of nitrogen, and stirred at room temperature for 18 hours. The solvent was removed by rotary evaporation under reduced pressure. The crude product was purified by silica-gel column chromatography (dichloromethane/methanol=20:1) to obtain light yellow oil, i.e., the target (R)-19, yield: 61%. $^1$H NMR (400 MHz, CDCl$_3$) δ 8.78 (s, 2H), 8.71 (s, 1H), 8.35 (d, J=7.7 Hz, 1H), 8.18 (s, 1H), 7.99 (d, J=7.7 Hz, 1H), 7.69 (d, J=7.9 Hz, 1H), 7.58 (dt, J=11.2, 8.8 Hz, 3H), 7.45 (t, J=7.7 Hz, 1H), 7.03 (d, J=9.7 Hz, 1H), 6.53 (s, 1H), 3.03 (t, J=7.2 Hz, 2H), 2.41 (t, J=7.1 Hz, 2H), 2.22 (s, 6H), 1.88-1.77 (m, 2H). $^{13}$C NMR (101 MHz, CDCl$_3$) δ 161.89, 159.26, 157.73, 141.82, 140.78, 137.46, 136.33, 132.46, 130.34, 130.19, 129.83, 129.78, 129.65, 128.88, 128.68, 127.70, 127.39, 118.55, 113.41, 57.89, 56.19, 45.27, 31.75, 27.01. HPLC purity: 96.8%, retention time: 16.83 min. HRMS (ESI) m/z C$_{28}$H$_{25}$D$_3$N$_6$OS [M+H]$^+$, calculated 500.2306; found 500.2293. 92.6% ee. Daicel OD column (0.46×25 cm), n-hexane/ethanol=80/20, 0.5 mL/min, λ=254 nm, t$_R$=28.96 (R), t$_S$=31.90 (S).

Compound (S)-18 was prepared with a similar method.

Embodiment 7: Anti-Tumor Compound 19

Anti-tumor compound 19, the structural formula of which is shown as below, and the synthesis steps of which are as below:

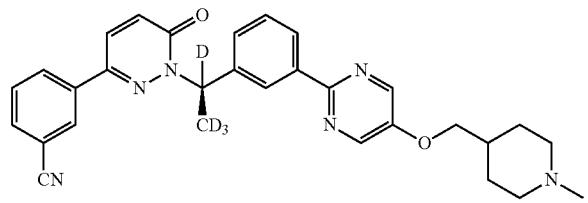 [SMILES: [2H][C@@](C)(c1cccc(-c2ncc(OCC3CCN(C)CC3)cn2)c1)n1nc(-c2cccc(C#N)c2)ccc1=O]

Structural formula of compound 19

The preparation of the intermediate 12 is the same as that in Embodiment 5; Except for using sodium formate as the reducing agent in the preparation of the intermediate (S)-13b, other processes are the same as in the process of Embodiment 5.

$^1$H NMR (500 MHz, CDCl$_3$) δ 8.65 (s, 1H), 8.48 (s, 2H), 8.26 (d, J=7.6 Hz, 1H), 8.18 (s, 1H), 7.96 (d, J=8.0 Hz, 1H), 7.67 (d, J=7.6 Hz, 1H), 7.60-7.50 (m, 3H), 7.41 (t, J=7.7 Hz, 1H), 7.00 (d, J=9.6 Hz, 1H), 6.52 (s, 1H), 3.94 (d, J=5.8 Hz, 2H), 2.90 (d, J=11.3 Hz, 2H), 2.28 (s, 3H), 1.97 (t, J=11.5 Hz, 2H), 1.85 (d, J=12.9 Hz, 3H), 1.46 (td, J=12.8, 6.6 Hz, 2H). 13C NMR (126 MHz, CDCl$_3$) δ 159.26, 157.28, 151.68, 143.92, 141.79, 140.63, 137.87, 136.35, 132.43, 130.29, 129.84, 129.74, 129.64, 129.36, 128.76, 128.66, 127.21, 126.94, 118.59, 113.38, 73.32, 56.19, 55.30, 46.43, 35.24, 28.91.

HRMS (ESI) m/z C$_{30}$H$_{28}$D$_3$N$_6$O$_2$[M+H]$^+$, calculated 510.2691; found 510.2682. HPLC purity: 98.60%, retention time: 15.17 min. 97.1% ee. Daicel AD column (0.46×25 cm), n-hexane/ethanol=80/20, 0.5 mL/min, λ=254 nm, tR=42.61 (R), tS=63.30 (S).

Test Example: Anti-Tumor Activities of the Novel Pyrimidine Derivatives of the Present Invention The novel pyrimidine derivatives of the invention were tested on their anti-tumor activities. Human highly metastatic hepatoma cells MHCC-97H were employed in the MTT process to evaluate the anti-tumor cell proliferation activities. The specific operation steps were as below: tumor cells were inoculated in a 96-well plate by a certain number of cells, at a cell density of 5×10$^3$-10×10$^3$/well. They were incubated in an incubator at 37° C. and a carbon dioxide concentration of 5% overnight, into which was then added the compound samples to be tested. After incubation for 72 hours, MTT was added to keep on for 4 hours, and dissolved with the addition of DMSO with shaking, and then detected with a microplate reader (570 nm).

Median inhibitory concentration IC$_{50}$ values of the novel pyrimidine derivatives of the invention on human highly metastatic hepatoma cells MHCC-97H are as shown in Table 1. It is indicated from the data in Table 1 that, the introduction of a chiral center in the molecule has great effects on the anti-tumor activities of the compound. The anti-tumor activities of the two enantiomers are significantly different. For example, the racemate (±)-5b (No. 4) inhibits the activity of human highly metastatic hepatoma cells MHCC-97H, the IC$_{50}$ of which is 0.0353 μM, while IC$_{50}$ of (R)-5b (No. 5) for inhibiting this tumor cell is 0.0037 μM, being superior to that of the racemate and Tepotinib (No. 14, its activity is 0.0134 μM). Accordingly, the inhibitory activity of (S)-5b (No. 6) is 0.1182 μM, much lower than that of the racemate and (R)-5b (No. 5). The activity of the compound (R)-5b for inhibiting tumor cells is 9.5 and 31.9 times that of (±)-5b and (S)-5b, respectively. As it can be seen that, the introduction of a chiral center at the position between pyridazinone and benzene ring plays an important role in enhancing the inhibition on the activity of human highly metastatic hepatoma cells MHCC-97H. There are similar structure-function relationships in other compounds. For example, in other three series, (±)-5a, (R)-5a and (S)-5a; (±)-6f, (R)-6f and (S)-6f; as well as (±)-7j, (R)-7j and (S)-7j, the compounds in (R)-configuration have better tumor cell inhibitory activities than the corresponding racemates (±) and compounds in (S)-configuration. It is demonstrated from the above results that, the spatial configuration of compounds in (R)-configuration plays an important role in inhibiting the activities of human highly metastatic hepatoma cells MHCC-97H.

The metabolic stability of a compound is a particularly important index of drug-like properties, and an important factor in determining whether a compound has the potential to become medicine. The new extracted SD rat liver microsomes were used to study the metabolic stabilities of the compounds (R)-5b and (R)-14. Firstly, a SD rat (200-300 g) was fasted for 12 hours, and then infused rapidly with normal saline. Liver was taken out from the rat, from which liver microsomes were extracted at 0-4° C., ready for use after calibrating the concentration of liver microsomes. At 37° C., liver microsomes were incubated in combination with a certain concentration of compounds and auxiliary reagents for a period of time. The reaction was then quenched with acetonitrile. High performance liquid chromatography was used to determine the contents of compounds (R)-5b and (R)-14. Prior to determining the metabolic stability of compounds in liver microsome of SD rats, the activity of liver microsome of SD rats was firstly tested by the same test method with the compound testosterone as the positive control compound; furthermore, Tepotinib was used as the control compound. Hydrogen atoms on the chiral central carbon and hydrogen atoms on the methyl of the compound (R)-5b were all substituted with its isotope deuterium to obtain a deuterated compound (R)-14. The compound (R)-14 has a better metabolic stability than (R)-5b while retaining good performance of (R)-5b on inhibiting the activity of tumor cells. As shown in Table 2 below, the metabolic half-life of (R)-5b in liver microsomes is 26.8 minutes, while the metabolic half-life of the compound (R)-14 is 35 minutes, both higher than the metabolic half-life of Tepotinib in liver microsomes (20.7 minutes), with improvements in stabilities. It has positive significance for improving the efficacy of anti-tumor compounds in vivo.

Studies on pharmacokinetic properties of the present novel pyrimidine derivatives in mice:

Shanghai Medicilon Bio-pharmaceutical Co., LTD was commissioned to research pharmacokinetic properties of the novel pyrimidine derivatives (R)-14, (R)-5b, and Tepotinib in mice. The specific processes are: An appropriate amount of the compounds (R)-14, (R)-5b and Tepotinib were accurately weighed and dissolved in a solution containing 2% Solutol and 98% 100 mM sodium acetate to obtain a clear dosing solution at a concentration of 2 mg/mL for intravenous administration. An appropriate amount of the compounds (R)-14, (R)-5b were accurately weighed and dissolved in 5% Solutol and 95% saline to obtain a clear dosing solution at a concentration of 5 mg/mL. An appropriate amount of Tepotinib was accurately weighed and dissolved in 5% Solutol, 5% DMSO and 90% saline, for oral administration and injection. Blood was collected from the test SD rats via jugular vein puncture, about 0.3 mL for per sample, and using heparin sodium as the anticoagulant. The time points for blood sampling were as below (including intravenous injection and oral administration): before administration, 5 min, 15 min, 30 min, 1 h, 2 h, 4 h, 8 h and 24 h post administration. After collection, blood samples were placed on ice, and plasma was separated by centrifugation within 30 minutes (centrifugation conditions: 8000 rpm, 6 minutes, 2-8° C.). The collected plasma was stored at −80° C. before analysis. Plasma samples were all analyzed qualitatively and quantitatively by LC-MS/MS. The dosage and ways for administration were intravenous injection (IV, 2 mg/kg) and intragastric administration (PO, 5 mg/kg) respectively, with the pharmacokinetic data shown in Table 3. As shown in Table 3, the clearance rates (CL) of the compounds (R)-14, (R)-5b are 819.12 mL/h/kg and 932.87 mL/h/kg respectively, much less than that of Tepotinib (3554.03 mL/h/kg); the drug exposure value (AUC) of the compounds (R)-14 and (R)-5b for intravenous injection (IV) and intragastric administration (PO) are 2441.64 h ng/mL (IV), 6309.37 h ng/mL (PO) and 2143.91 h ng/mL (IV), 4580.23 h ng/mL (PO) respectively, greatly higher than those of the positive drug Tepotinib (562.74 h ng/mL (IV) and 981.69 h ng/mL (PO)). Furthermore, the half-life ($T_{1/2}$) of the compounds (R)-14 and (R)-5b are 4.48 and 4.23 hours respectively, significantly superior that of Tepotinib (1.79 hours). This result is consistent with the results of previous experiments on the stability of rat liver microsomes, indicating that the compounds (R)-14, (R)-5b have better in vivo stability than Tepotinib. Finally, the bioavailabilies of the compounds (R)-14, (R)-5b are 103.73% and 85.97% respectively, higher than that of the positive drug Tepotinib (67.77%). Overall, it is demonstrated from the study on pharmacokinetic properties in mice that, compared with the positive drug Tepotinib, the novel pyrimidine derivatives (R)-14 and (R)-5b have lower clearance rates, higher drug exposure value, longer metabolic half-life in the body, and higher bioavailability. These results fully demonstrate that, due to the introduction of a chiral structure, the novel pyrimidine derivatives (R)-14 and (R)-5b do have great improvements in terms of anti-tumor cell activities and pharmacokinetic properties compared to the positive drug Tepotinib. It can be seen from further comparing the pharmacokinetic properties of the compounds (R)-14 and (R)-5b, due to introducing an isotope of hydrogen (deuterium) with more stable chemical properties at the key site, (R)-14 has better pharmacokinetic properties in mice, more meeting the requirements of being medicine.

TABLE 1

The activity of the present novel pyrimidine derivatives on inhibiting human highly metastatic hepatoma cell MHCC-97H

| No. | Structural formula of compounds | Human highly metastatic hepatoma cell MHCC-97H (μM) |
|---|---|---|
| 1 | 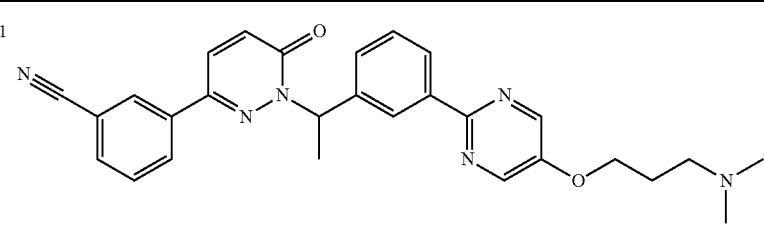<br>(±)-5a | 0.0476 |
| 2 | 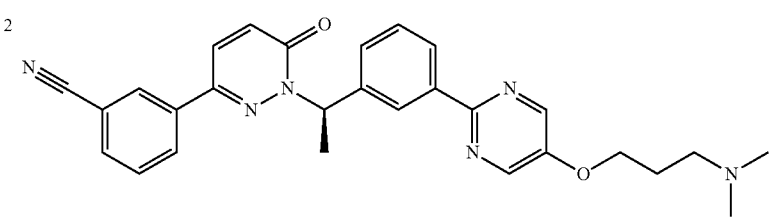<br>(R)-5a | 0.0140 |

TABLE 1-continued

The activity of the present novel pyrimidine derivatives on inhibiting human highly metastatic hepatoma cell MHCC-97H

| No. | Structural formula of compounds | Human highly metastatic hepatoma cell MHCC-97H (μM) |
|---|---|---|
| 3 | (S)-5a | 1.0415 |
| 4 | (±)-5b | 0.0353 |
| 5 | (R)-5b | 0.0037 |
| 6 | (S)-5b | 0.1182 |
| 7 | (±)-6f | 0.0272 |

TABLE 1-continued

The activity of the present novel pyrimidine derivatives on inhibiting human highly metastatic hepatoma cell MHCC-97H

| No. | Structural formula of compounds | Human highly metastatic hepatoma cell MHCC-97H (μM) |
|---|---|---|
| 8 | (R)-6f | 0.0139 |
| 9 | (S)-6f | 0.1890 |
| 10 | (±)-7j | 0.0270 |
| 11 | (R)-7j | 0.0117 |
| 12 | (S)-7j | 0.4150 |

TABLE 1-continued
The activity of the present novel pyrimidine derivatives on inhibiting human highly metastatic hepatoma cell MHCC-97H
| No. | Structural formula of compounds | Human highly metastatic hepatoma cell MHCC-97H (μM) |
|---|---|---|
| 13 | 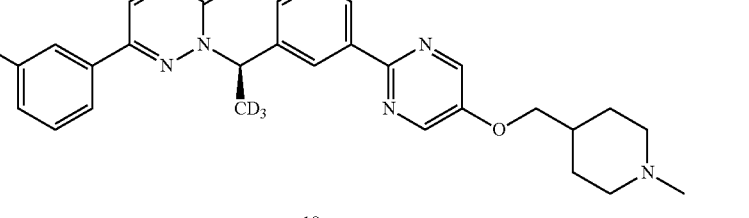<br>18 | 0.0035 |
| 14 | 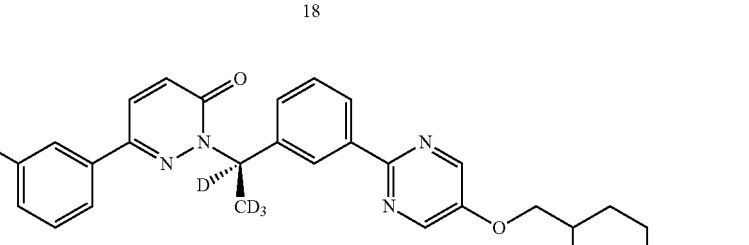<br>(R)-14 | 0.0037 |
| 15 | 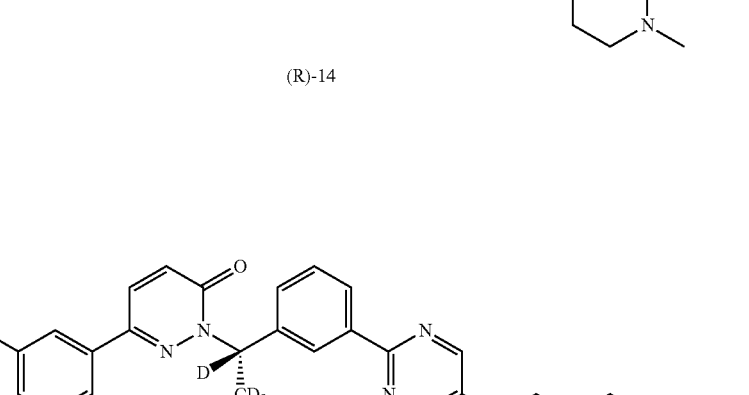<br>(S)-14 | 1.117 |
| 16 | 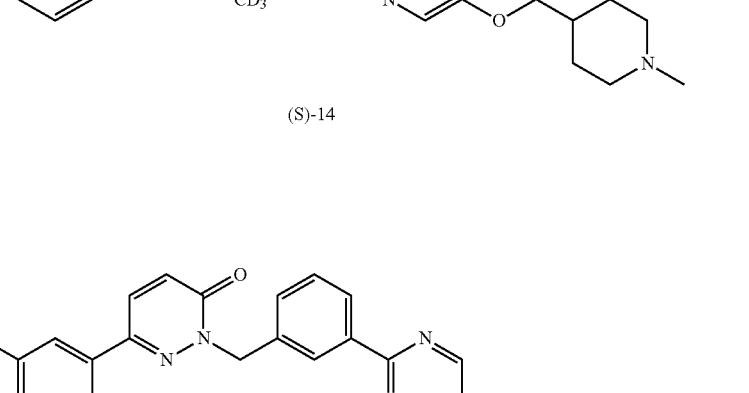<br>Tepotinib | 0.0134 |

TABLE 2

Test on the stability of rat liver microsomes

| compd | K (min$^{-1}$) | T$_{1/2}$ (min)$^a$ |
|---|---|---|
| testosterone$^b$ | 0.3013 | 2.3 |
| (R)-5b | 0.0259 | 26.8 |
| (R)-14 | 0.0198 | 35.0 |
| Teponinib | 0.0134 | 20.7 |

TABLE 3

Pharmacokinetic data of the compounds (R)-5b, (R)-14 and Tepotinib in mice

| | PK parameters | (R)-14 | (R)-5b | Tepotinib |
|---|---|---|---|---|
| IV 2 mg/kg | CL (mL/h/kg) | 819.12 | 932.87 | 3554.03 |
| | V$_z$ (mL/kg) | 5289.04 | 5687.11 | 9178.68 |
| | AUC$_{0-\infty}$ (h · ng/mL) | 2441.64 | 2143.91 | 562.74 |
| | T$_{1/2}$ (h) | 4.48 | 4.23 | 1.79 |
| PO 5 mg/kg | C$_{max}$ (ng/mL) | 613.84 | 495.30 | 211.23 |
| | T$_{max}$ (h) | 4 | 2 | 1 |
| | AUC$_{0-\infty}$ (h · ng/mL) | 6309.37 | 4580.23 | 981.69 |
| | F % | 103.73 | 85.97 | 67.77 |

IV = intravenous injection,
PO = intragastric administration.

Embodiment 8: Synthesis of (R)-1D228

(1) Preparation of the intermediate 2: an aqueous solution of sodium carbonate (sodium carbonate 132 mmol, 13.468 g, 65 mL water) was added into a solution of 5-fluoro-2-chloropyrimidine (66 mmol, 8.71 g) in toluene (130 mL), into which were then added bis(triphenyl phosphine)palladium chloride (1.365 mmol, 0.962 g), acetyl phenyl boronic acid (64 mmol, 10.50 g), and ethanol (65 mL). Under nitrogen protection, the reaction was stirred at 83° C. for 11 h, and cooled to room temperature. 160 mL ethyl acetate and water (40 mL) were added into the reaction system to separate out the organic phase. The water phase was extracted with 40 mL ethyl acetate once. The organic phase was combined, washed with saturated brine, dried over anhydrous sodium sulfate. The solvent was removed. The crude product was added into ethyl acetate:petroleum ether (1:8), pulped, filtered and dried to get a light yellow solid 11.31 g. Yield 81.8%.

HR (400 MHz, CDCl$_3$), δ 8.98 (t, J=1.6 Hz, 1H), 8.70 (s, 2H), 8.59 (s, 1H), 8.09 (s, 1H), 7.60 (s, 1H), 2.71 (s, 3H).

(2) Preparation of the intermediate (S)-13:

a) Preparation of a chiral catalyst: Dichloro(4-methyl isopropyl benzene)ruthenium (II) dimer (0.06 mmol, 37 mg), and a chiral ligand (S, S)-CsDPEN (0.13 mmol, 56 mg) were placed in a 150 mL reaction flask, into which was added water (6 mL) and stirred at 40° C. under nitrogen protection for 4 hours to prepare the catalyst, ready for use.

b) Reaction of the intermediate 2 and 1-methyl piperidine-4-methanol: At 0° C., sodium hydride (60%, 1.5 equ, 3.76 g) was added batchwise into a solution of 1-methyl piperidine-4-methanol (1.2 equ, 60 mmol, 7.75 g) in N,N-dimethyl formamide (100 mL), and stirred for 15 minutes. Then a solution of the intermediate 2 (50 mmol, 10.8 g) in DMF (130 mL) was added dropwise into the above mixture while keeping the reaction temperature (0° C.) basically the same. After dropwise addition, the reaction mixture was slowly warmed to room temperature. Upon the completion of reaction monitored by TLC (about 1.5 hours), the reaction solution was slowly poured into 300 mL water (with stirring), into which was added an appropriate amount of dichloromethane and stirred to separate the lower layer. The upper layer was extracted with dichloromethane. After the extraction was completed upon TLC detection, the total used amount of dichloromethane was about 400 mL. The organic phase was combined, washed with water (3*50 mL) to remove DMF as far as possible, and washed with saturated brine to obtain about 400-450 mL solution of the intermediate in dichloromethane, which was kept under nitrogen protection for use.

C) Under nitrogen protection, the above solution of the intermediate in dichloromethane was added into the prepared chiral catalyst solution, into which was then added an aqueous solution of deuterated sodium formate (10. 2 g, 50 mL water, about 3 equ) under nitrogen protection. The reaction was stirred at room temperature for 10 hours, until the completion of the reaction detected by TLC. 200 mL water was added into the reaction system and stirred to separate the lower layer. The water layer was extracted twice with an appropriate amount (100 mL) of dichloromethane. The organic phase was combined, washed with saturated brine, dried over anhydrous sodium sulfate, filter over a silica gel column (dichloromethane:methanol, 10:1) and eluted to get the intermediate (S)-13, enantiomeric excess (ee) determined by HPLC, 98% ee. Analytical conditions: AD-H column, mobile phase, isopropanol 25%, n-hexane 75% (added with 0.1% of diethylamine). The chemical purity of the intermediate (S)-13 was greater than 95%.

(3) Synthesis of target (R)-1D228: To a reaction flask were added 3-(6-oxo-1,6-dihydropyridazin-3-yl)-benzonitrile (22 mmol, 4.41 g), the intermediate (S)-13 (20 mmol, 6.54 mg), triphenylphosphine (40 mmol, 10.5 g), and tetrahydrofuran (100 mL, with a water content not greater than 30-50 ppm), and stirred at 0° C. under nitrogen protection for 10 minutes. Diisopropyl azodicarboxylate (8.08 g, 40 mmol) was slowly added dropwise, warmed naturally to room temperature, and reacted overnight. 200 mL ethyl acetate and 100 mL water were added into the reaction system, stirred and filtered to separate out the organic layer. The water layer was extracted with 100 mL ethyl acetate. The organic phase was filtered over 60 g silica gel, and washed with ethyl acetate until no chromogenic substance was detected by TLC under ultraviolet light. Then it was eluted with ethyl acetate/petroleum ether/triethylamine (200/50/2). The eluent was collected, detected by TLC, and then concentrated to get the target product. Analytical conditions for optical purity: Daicel ADH column (0.46×25 cm), n-hexane (added with one thousandth of diethylamine)/ethanol=80/20, 0.5 mL/min, λ=254 nm, tR=40.66 (R), tS=64.22 (S). Analytical conditions for chemical purity: ace column, CH$_3$CN:H$_2$O:triethylamine=70:30:0.1.1H NMR (400 MHz, CDCl$_3$) δ 8.67 (t, J=1.6 Hz, 1H), 8.50 (s, 2H), 8.28 (d, J=7.8 Hz, 1H), 8.20 (s, 1H), 7.98 (d, J=8.0 Hz, 1H), 7.69 (d, J=7.8 Hz, 1H), 7.56 (m, 3H), 7.43 (t, J=7.7 Hz, 1H), 7.02 (d, J=9.7 Hz, 1H), 3.96 (d, J=5.9 Hz, 2H), 2.92 (d, J=11.4 Hz, 2H), 2.30 (s, 3H), 1.97 (m, 2H), 1.93-1.82 (m, 6H), 1.52-1.41 (m, 2H). 13C NMR (101 MHz, CDCl3) δ 159.22, 157.30, 151.70, 143.94, 141.78, 140.58, 137.89, 136.38, 132.42, 130.29, 129.82, 129.73, 129.64, 129.35, 128.75, 128.64, 127.23, 126.94, 118.57, 113.41, 73.36, 55.32, 46.44, 35.27, 28.94, 19.91.

HRMS (ESI) m/z C$_{30}$H$_{29}$D1N$_6$O$_2$[M+H]$^+$, calculated: 508.2566; found 508.2553. HPLC purity: 99.0%, retention time: 15.03 min. 97.1% ee. Daicel AD column (0.46×25 cm), n-hexane/ethanol=80/20, 0.5 mL/min, λ=254 nm, tR=40.66 (R), tS=64.22 (S).

Embodiment 9: In Vitro and In Vivo Anti-Tumor Activities of (R)-1D228

(1) The anti-tumor cell activities of (R)-1D228 are tested. With Tepotinib and (R)-4D288 as the control, human highly metastatic hepatoma cell MHCC-97Hwas selected to evaluate the antitumor cell proliferative activities through the MTT process. The specific operation steps were as below: the tumor cells were inoculated in a 96-well culture plate following a certain number of cells, the cell density was $5\times10^3$-$10\times10^3$/well. After cultivation in an incubator at 37° C. and at a CO2 concentration of 5% overnight, the compound samples to test were added. After cultivation for 72 hours, MTT was added to continue the cultivation for 4 hours. DMSO was then added to dissolve with stirring, and detected with a microplate reader (570 nm). The obtained results are shown in Table 4:

(2) Anti-tumor tests of (R)-ID228 and (R)-4D288 are conducted in naked mice, the testing procedures are shown in Table 5:

TABLE 5

Anti-tumor testing procedures in naked mice

| Group No. | Number of Animals | | Names of Subjects or Control Substances | Dosage (mg/kg) | Concentration of Subject (mg/mL) | Dose Volume (mL/kg) |
|---|---|---|---|---|---|---|
| | Female | Male | | | | |
| A | 0 | 6 | Vehicle | — | — | 10 |
| B | 0 | 6 | tepotinib | 8 | 0.8 | 10 |

TABLE 4

Inhibitory activities of (R)-1D228 on human highly metastatic hepatoma cell MHCC-97H

| No. | Structural formula of compounds | Human highly metastatic hepatoma cell MHCC-97H (μM) |
|---|---|---|
| 1 | (R)-1D228 | 0.0033 |
| 2 | (R)-14 | 0.0037 |
| 3 | Tepotinib | 0.0134 |

TABLE 5-continued

Anti-tumor testing procedures in naked mice

| Group No. | Number of Animals Female | Number of Animals Male | Names of Subjects or Control Substances | Dosage (mg/kg) | Concentration of Subject (mg/mL) | Dose Volume (mL/kg) |
|---|---|---|---|---|---|---|
| C | 0 | 6 | 1D228 | 8 | 0.8 | 10 |
| D | 0 | 6 | 1D228 | 4 | 0.4 | 10 |
| E | 0 | 6 | 4D228 | 8 | 0.8 | 10 |
| F | 0 | 6 | 4D228 | 4 | 0.4 | 10 |

Wherein: A, B, C, D, E, F represents model control group, Tepotinib control group, (R)-1D228 I, II, (R)-4D288 I, II groups, respectively.

Route of administration: intragastric administration, at 10 mL/kg;

Frequency and duration of administration: For model control group, Tepotinib control group and each dose group of (R)-1D228 and (R)-4D288, administration once a day for 2 weeks.

Figure 6:
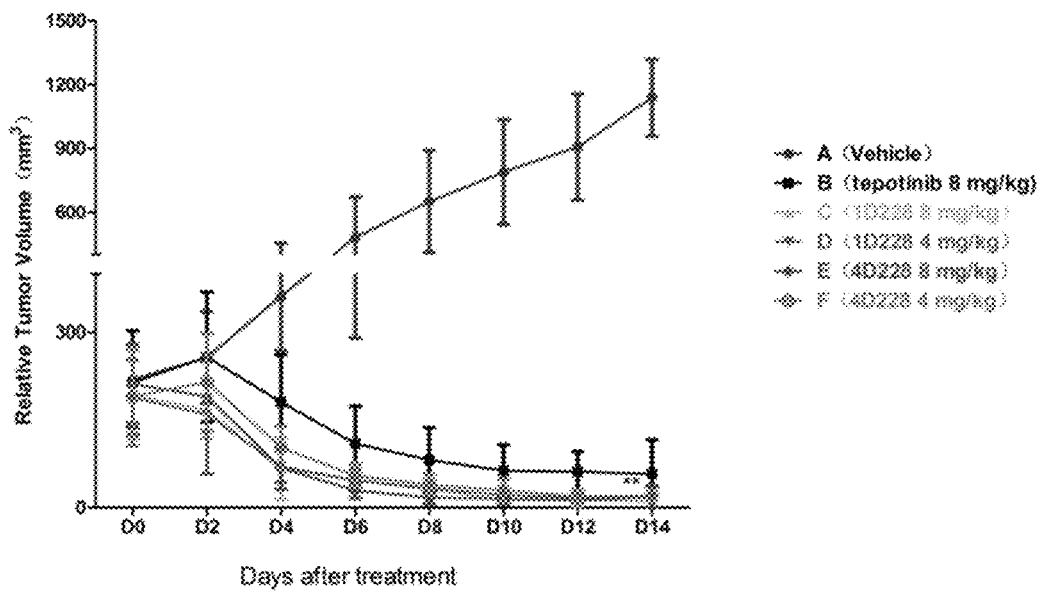
FIG. 6 shows the inhibition profile of tumor growth in each experimental group of Embodiment 9.
Figure 7:
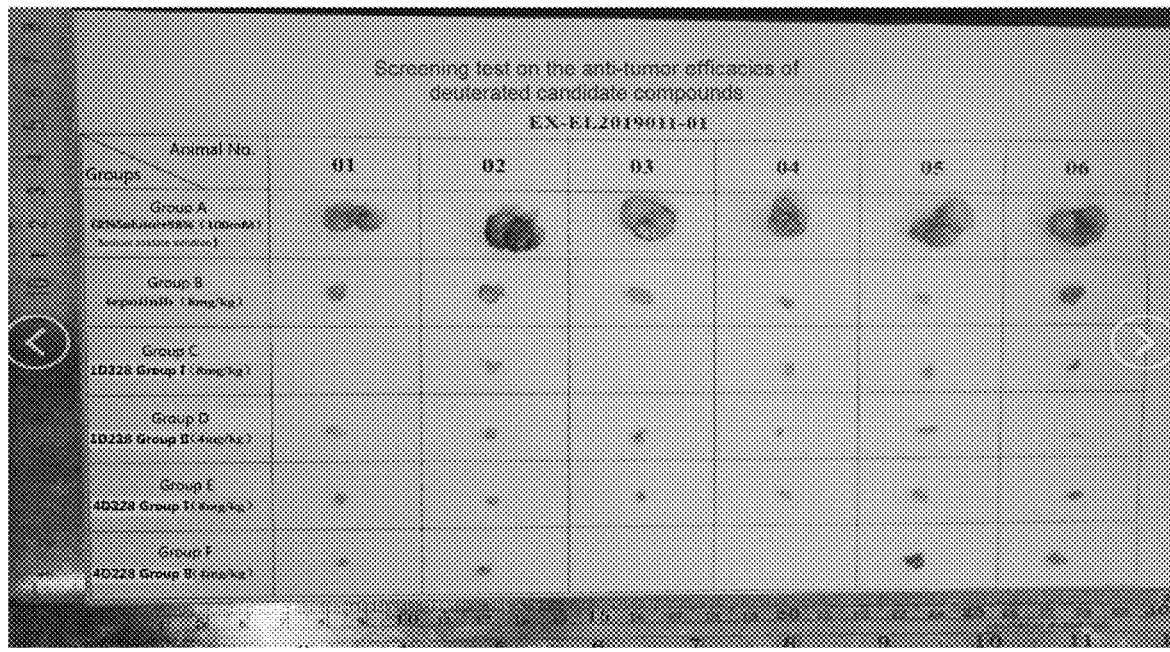
FIG. 7 is a diagram showing the tumor anatomy of animals in each group of Embodiment 9.
Figure 8:
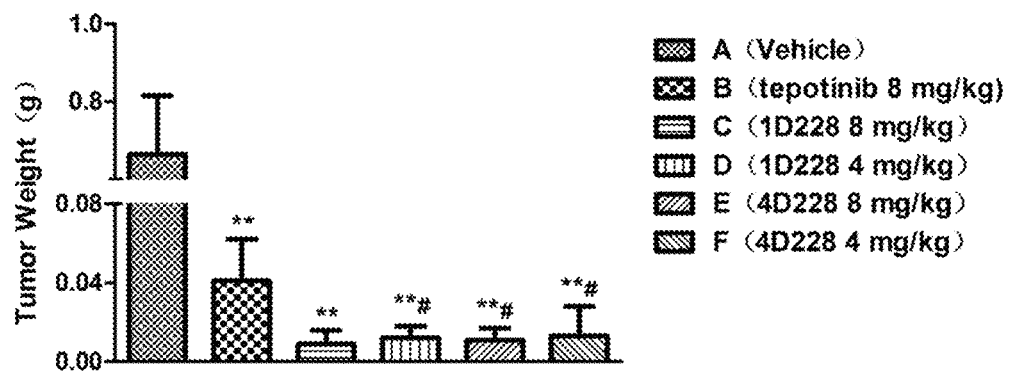
FIG. 8 is a diagram showing the tumor weights in each group of Embodiment 9.

The inhibition profile of tumor growth in each experimental group is shown in FIG. 6;

The tumor anatomy of animals in each group is shown in FIG. 7;

The tumor weights of each group are shown in FIG. 8;

The statistical results of tumor weights, tumor inhibition rates, and relative tumor proliferation rates in each group are shown in Table 6:

TABLE 6

Statistical results of tumor weights, tumor inhibition rates, and relative tumor proliferation rates in each group

| Groups | N | Tumor weights | Tumor inhibition rate (%) | Relative tumor proliferation rate T/C (%) |
|---|---|---|---|---|
| A (Model control group, Vehicle) | 6 | 0.664 ± 0.151 | — | — |
| B (tepotinib, 8 mg/kg) | 6 | 0.041 ± 0.021** | 93.8 | 4.9 |
| C (1D228, 8 mg/kg) | 6 | 0.009 ± 0.007**# | 98.6 | 1.17 |
| D (1D228, 4 mg/kg) | 6 | 0.011 ± 0.006**# | 98.3 | 1.78 |
| E (4D228, 8 mg/kg) | 6 | 0.012 ± 0.006**# | 98.2 | 1.59 |
| F (4D228, 4 mg/kg) | 6 | 0.013 ± 0.015**# | 98.0 | 2.28 |

Figure 9:
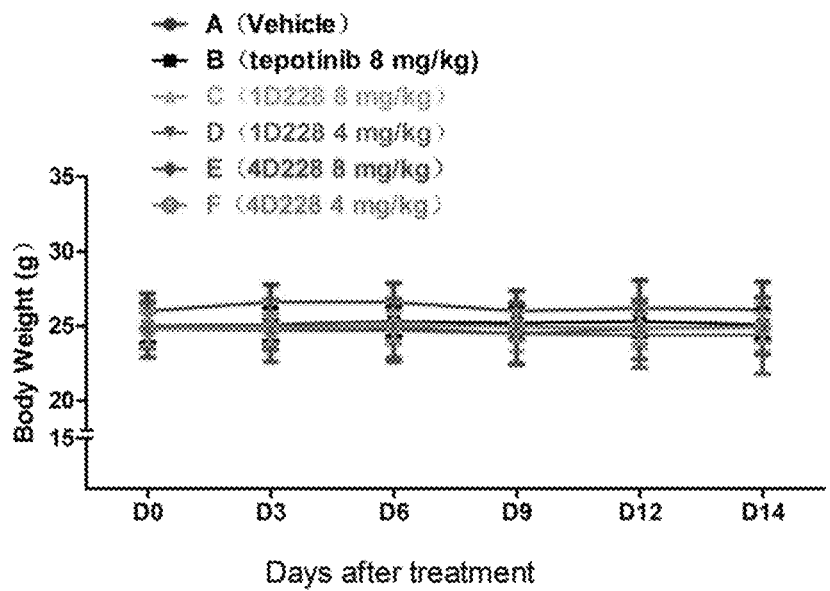
FIG. 9 is a diagram showing the body weight changes of animals in each group of Embodiment 9 during administration.

The body weights of animals in each group during administration are shown in FIG. 9 and Table 7, showing that there were no significant changes in the body weights of mice and there were not abnormal behaviors of mice during administration.

As can be seen from the above results, the tumor weights in the (R)-1D228 intragastric administration groups at dosages of 8 and 4 mg/kg are lower than that in the model control group (P<0.01), and the tumor inhibition rates are 98.6% and 98.3%, respectively. Additionally, the inhibition effect on the tumor growth in the (R)-1D228 intragastric administration group at a dosage of 4 mg/kg is superior to that in the tepotinib intragastric administration group at a dosage of 8 mg/kg, 93.8%.

Compared with (R)-4D288 containing 4 deuterium atoms (the tumor inhibition rates are 98.2% and 98.0%, respectively), (R)-1D228 has a tumor inhibition rate not lower than (slightly higher than) that of (R)-4D288, but the cost is greatly reduced.

The foregoing description is only the preferred implementation of the disclosure. It should be noted that several improvements and modifications can be made to the disclosure by persons with ordinary skills in the art without deviating from the principle of the disclosure, which should also be considered as the scope of the disclosure.

What is claimed is:

1. A pyrimidine derivative of Formula 2, a pharmaceutically acceptable salt thereof, or a pharmaceutical solvate thereof:

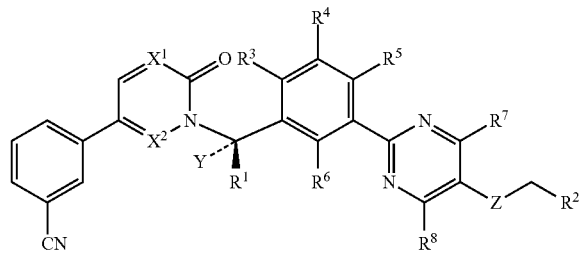

Formula 2 wherein $X^1$ is CH; $X^2$ is N; Y is deuterium; $R^1$ is an alkyl containing one carbon; Z is oxygen; $R^2$ is 4-piperidyl with the nitrogen atom attached to an alkyl containing one carbon; and each of $R^3$-$R^8$ is hydrogen.

2. A process for preparing the pyrimidine derivative according to claim 1, comprising the steps of:
(1) conducting a chiral hydrogen transfer reaction between the compound of Formula 13 and deuterated sodium formate in the presence of dichloro (p-cymene)

TABLE 7

Statistics of body weights of animals in each group during administration

| Groups | D 0 | D 3 | D 6 | D 9 | D 12 | D 14 |
|---|---|---|---|---|---|---|
| A (Vehicle) | 26.0 ± 1.2 | 26.6 ± 1.2 | 26.6 ± 1.3 | 26.0 ± 1.4 | 26.2 ± 1.9 | 26.1 ± 1.9 |
| B (tepotinib, 8 mg/kg) | 24.9 ± 1.0 | 25.1 ± 1.1 | 25.3 ± 1.0 | 25.2 ± 1.1 | 25.3 ± 1.0 | 25.1 ± 1.0 |
| C (1D228, 8 mg/kg) | 24.9 ± 1.3 | 25.0 ± 1.5 | 25.2 ± 1.4 | 24.9 ± 1.6 | 24.9 ± 1.4 | 24.9 ± 1.6 |
| D (1D228, 4 mg/kg) | 25.0 ± 1.5 | 25.1 ± 1.7 | 24.9 ± 2.0 | 24.5 ± 2.1 | 24.4 ± 2.2 | 21.4 ± 9.6 |
| E (4D228, 8 mg/kg) | 24.8 ± 1.9 | 24.7 ± 2.1 | 24.7 ± 2.1 | 24.5 ± 2.0 | 24.8 ± 2.0 | 25.0 ± 1.9 |
| F (4D228, 4 mg/kg) | 24.8 ± 1.1 | 24.8 ± 1.0* | 25.0 ± 1.0* | 25.0 ± 1.0 | 24.8 ± 1.0 | 24.9 ± 1.0 | ruthenium (II) dimer and (S,S)-CsDPEN to obtain deuterated intermediate (S)-13, in which Formula 13 is Formula 13

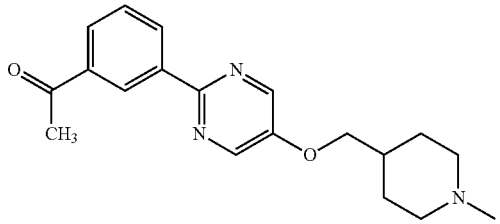

and deuterated intermediate (S)-13 is

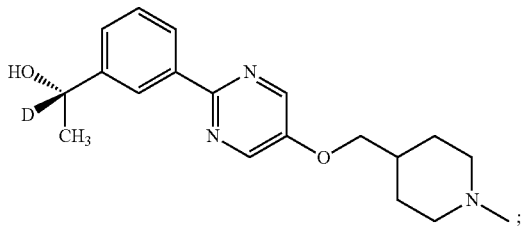 [SMILES: [2H][C@@](C)(O)c1cccc(-c2ncc(OCC3CCN(C)CC3)cn2)c1]

and (2) conducting a Mitsunobu reaction between deuterated intermediate (S)-13 and cyano-carrying pyridazinone having the structure of

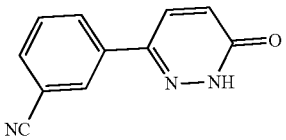

to obtain the pyrimidine derivative of Formula 2.

3. The process according to claim 2, wherein, in step (1), the molar ratio of the compound of Formula 13, deuterated sodium formate, dichloro(p-cymene) ruthenium (II) dimer, and (S,S)-CsDPEN is (1.0 to 5.0):(5.0 to 25):(0.05 to 0.25): (0.10 to 0.5), the solvent is dichloromethane and water, the chiral hydrogen transfer reaction temperature is 25 to 35° C., and the chiral hydrogen transfer reaction time is 8 to 10 hours.

4. The process according to claim 2, wherein, in step (2), the Mitsunobu reaction is performed in a solvent at 0° C. to 4° C. for 15 to 30 minutes and then 25° C. to 40° C. for 18 to 24 hours in the presence of triphenylphosphine and diisopropyl azodicarboxylate; the molar ratio of deuterated intermediate (S)-13, the cyano-carrying pyridazinone, triphenylphosphine, and diisopropyl azodicarboxylate is (0.5 to 2.5):(0.5 to 2.5):(0.75 to 3.75):(0.75 to 3.75); and the solvent is tetrahydrofuran/N,N-dimethyl formamide at a mass ratio of 10:1.

5. A process for preparing the pyrimidine derivative according to claim 1, comprising the steps of:
(1) crosslinking intermediate 2 with 1-methylpiperidine-4-methanol in the presence of sodium hydride to obtain a reaction solution, in which intermediate 2 is

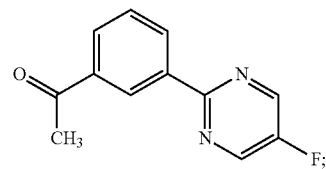 [SMILES: CC(=O)c1cccc(-c2ncc(F)cn2)c1]

extracting the reaction solution with dichloromethane to obtain a dichloromethane extraction phase; and reacting the dichloromethane extraction phase with deuterated sodium formate in the presence of dichloro(p-cymene) ruthenium (II) dimer and (S,S)-CsDPEN to obtain deuterated intermediate (S)-13; and (2) conducting a Mitsunobu reaction between deuterated intermediate (S)-13 and cyano-carrying pyridazinone having the structure of

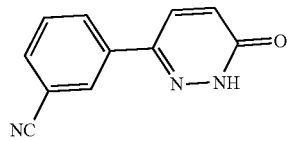 [SMILES: N#Cc1cccc(-c2ccc(=O)[nH]n2)c1]

to obtain the pyrimidine derivative of Formula 2.

6. The process according to claim 5, wherein intermediate 2 is prepared by reacting 2-chloro-5-fluoropyrimidine with 3-acetyl phenylboronic acid.

7. A pharmaceutical composition comprising a therapeutically effective amount of the pyrimidine derivative of claim 1 and a pharmaceutically acceptable adjuvant.

8. The pharmaceutical composition according to claim 7, wherein the pharmaceutical composition is in the form of an injection, a tablet, a capsule, a pill, a suspension, or an emulsion.

9. The pharmaceutical composition according to claim 7, wherein the pyrimidine derivative is the pharmaceutical solvate or the pharmaceutically acceptable salt of the pyrimidine derivative of Formula 2.

10. The pharmaceutical composition according to claim 8, wherein the pyrimidine derivative is the pharmaceutical solvate or the pharmaceutically acceptable salt of the pyrimidine derivative of Formula 2.

11. A method for treating a tumor, comprising administrating a therapeutically effective amount of the pyrimidine derivative of claim 1 to a subject in need thereof, wherein the tumor is hepatocellular carcinoma.

12. A method for treating a tumor, comprising administrating the pharmaceutical composition of claim 7 to a subject in need thereof, wherein the tumor is hepatocellular carcinoma.

13. The method of claim 12, wherein the pharmaceutical composition is administrated through oral administration, percutaneous injection, intravenous injection, or intramuscular injection.

* * * * *